US012709647B2

(12) United States Patent
Zhu et al.

(10) Patent No.: US 12,709,647 B2
(45) Date of Patent: Aug. 18, 2026

(54) MULTI-SPECIFIC ANTIBODIES AND METHODS OF USING THEREOF

(71) Applicants: SYSTIMMUNE, INC., Redmond, WA (US); BAILI-BIO (CHENGDU) PHARMACEUTICAL CO., LTD., Chengdu (CN)

(72) Inventors: Yi Zhu, Chengdu (CN); Ole Olsen, Everett, WA (US); Dong Xia, Redmond, WA (US); David Jellyman, Duvall, WA (US); Katrina Bykova, Seattle, WA (US); Anne-Marie K. Rousseau, Seattle, WA (US); Bill Brady, Bothell, WA (US); Blair Renshaw, Renton, WA (US); Brian Kovacevich, Snohomish, WA (US); Yu Liang, Redmond, WA (US); Zeren Gao, Redmond, WA (US)

(73) Assignee: SYSTIMMUNE, INC., Redmond, WA (US)

( * ) Notice: Subject to any disclaimer, the term of this patent is extended or adjusted under 35 U.S.C. 154(b) by 406 days.

(21) Appl. No.: 18/296,871

(22) Filed: Apr. 6, 2023

(65) Prior Publication Data

US 2023/0322920 A1 Oct. 12, 2023

Related U.S. Application Data

(62) Division of application No. 16/615,117, filed as application No. PCT/US2018/039153 on Jun. 22, 2018, now Pat. No. 11,649,286.

(60) Provisional application No. 62/524,554, filed on Jun. 25, 2017.

(51) Int. Cl.
*C07K 16/44* (2006.01)
*A61K 39/395* (2006.01)
*A61K 45/06* (2006.01)
*C07K 16/28* (2006.01)

(52) U.S. Cl.
CPC .......... *C07K 16/44* (2013.01); *A61K 39/3955* (2013.01); *A61K 45/06* (2013.01); *C07K 16/2803* (2013.01); *C07K 16/2809* (2013.01); *C07K 16/2827* (2013.01); *C07K 16/2863* (2013.01); *C07K 2317/31* (2013.01); *C07K 2317/55* (2013.01); *C07K 2317/622* (2013.01); *C07K 2317/73* (2013.01)

(58) Field of Classification Search
CPC .......................... A61K 39/3955; C07K 16/468
See application file for complete search history.

(56) References Cited

U.S. PATENT DOCUMENTS

2020/0157213 A1 5/2020 Zhu et al.

*Primary Examiner* — Elly-Gerald Stoica
(74) *Attorney, Agent, or Firm* — EpiMED LLC

(57) ABSTRACT

The application provides tri-specific antibody monomers having a N-terminal and a C-terminal, comprising in tandem from the N-terminal to the C-terminal, a first scFv domain at the N-terminal, a Fab domain, a Fc domain, and a second scFv domain at the C-terminal. In one embodiment, the first scFv domain, the Fab domain, and the second scFv domain each has a binding specificity against a different antigen.

18 Claims, 11 Drawing Sheets

Specification includes a Sequence Listing.

FIGURE 1 shows the example tri-specific antibodies used in binding and RTCC assays

| Antibody ID | Domain 1 | Humanized Variant | Domain 2 | Humanized Variant | IgG Fc | Domain 3 | Humanized Variant |
|---|---|---|---|---|---|---|---|
| | LH-scFv | | LH-scFv | | | HL-scFv | |
| SI-27X33 | R11 | - | 4420(FITC) | - | n2 | I2C | - |
| SI-27X39 | 323H7 | L1H4 | PL230C6 | H3L2 | n2 | I2C | - |
| SI-27X45 | 338H4 | L4H3 | PL230C6 | H3L2 | n2 | PL221 | H1L1 |
| SI-27X62 | R11 | - | PL230C6 | H3L2 | n2 | 4420(FITC) | - |
| SI-27X63 | 323H7 | L1H4 | PL230C6 | H3L2 | n2 | 284A10 | H1L1 |
| SI-27X69 | 338H4 | L4H3 | PL230C6 | H3L2 | n2 | 299F6 | H2L1 |
| SI-27X73 | 338H4 | L4H3 | PL230C6 | H3L2 | n2 | 480C8 | H2L1 |
| SI-27X75 | 4420(FITC) | - | PL230C6 | H3L2 | n2 | I2C | - |
| SI-27X109 | PL230C6 | L2H3 | 4420(FITC) | - | n2 | 480C8 | H2L1 |
| SI-37X1 | PL230C6 | L2H3 | 806 | - | n2 | 480C8 | H2L1 |
| SI-37X2 | 806 | - | PL230C6 | H3L2 | n2 | 480C8 | H2L1 |
| SI-37X3 | 4420(FITC) | - | 806 | - | n2 | 480C8 | H2L1 |
| SI-37X4 | PL230C6 | L2H3 | 806 | - | n2 | 4420(FITC) | - |
| SI-37X5 | 806 | - | 4420(FITC) | - | n2 | 480C8 | H2L1 |
| SI-37X6 | 806 | - | PL230C6 | H3L2 | n2 | 4420(FITC) | H2L1 |
| SI-37X7 | - | - | - | - | n2 | 480C8 | H2L1 |
| SI-34X2 | 21D4 | - | PL230C6 | H3L2 | n2 | 480C8 | H2L1 |
| SI-34X7 | 4420(FITC) | - | PL230C6 | H3L2 | n2 | 480C8 | H2L1 |
| SI-34X8 | 21D4 | - | 4420(FITC) | - | n2 | 480C8 | H2L1 |
| SI-34X9 | 21D4 | - | PL230C6 | H3L2 | n2 | 4420(FITC) | - |

FIGURE 2 shows the specificity of the antibody binding domains used in the example tri-specific antibodies

| Antibody Name | Specificity |
|---|---|
| 21D4 | CD19 |
| 806 | EGFRviii |
| 4420 | FITC |
| R11 | ROR1 Kringle Domain |
| 323H7 | ROR1 IgD Domain |
| 338H4 | ROR1 Frizzled Domain |
| PL230C6 | PD-L1 |
| I2C | CD3 complex Epsilon chain |
| 284A10 | CD3 complex Epsilon chain |
| 299F6 | CD3 complex Epsilon chain |
| 480C8 | CD3 complex Epsilon chain |

FIGURE 3 is a diagram showing a symmetric tri-specific antibody according to at least one embodiment.
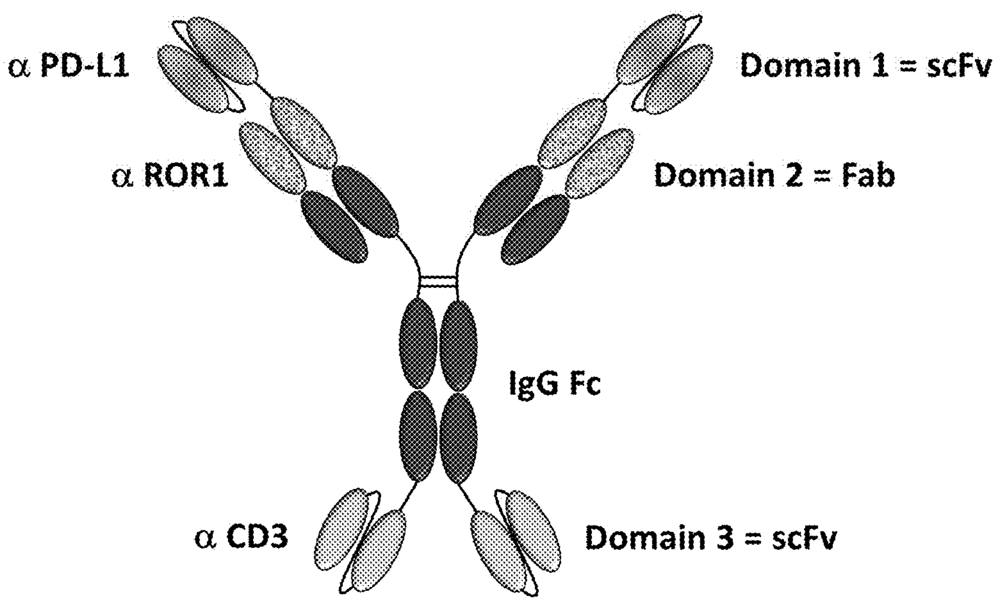

FIGURE 4 is a snapshot of experiment results showing FACS analysis of tri-specific antibodies binding to ROR1 expressing CHO cells according to some embodiments.
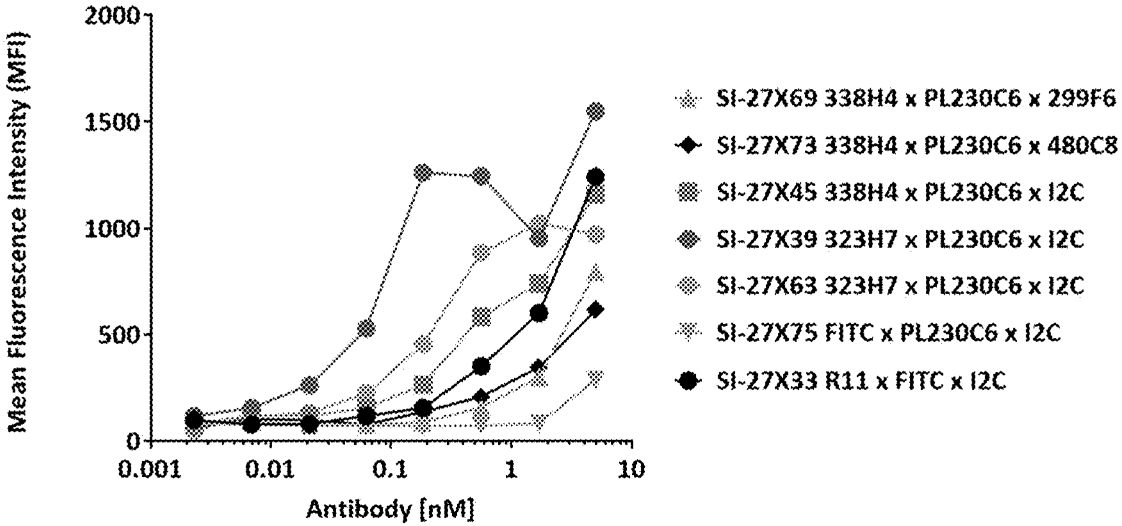
N.B: The binding domain 323H7 is specific for the Ig domain of ROR1 and the binding domain 338H4 is specific for the frizzled domain of ROR1

FIGURE 5 is a snapshot of experiment results showing FACS analysis of tri-specific antibody binding to PD-L1 expressing CHO cells according to some embodiments.
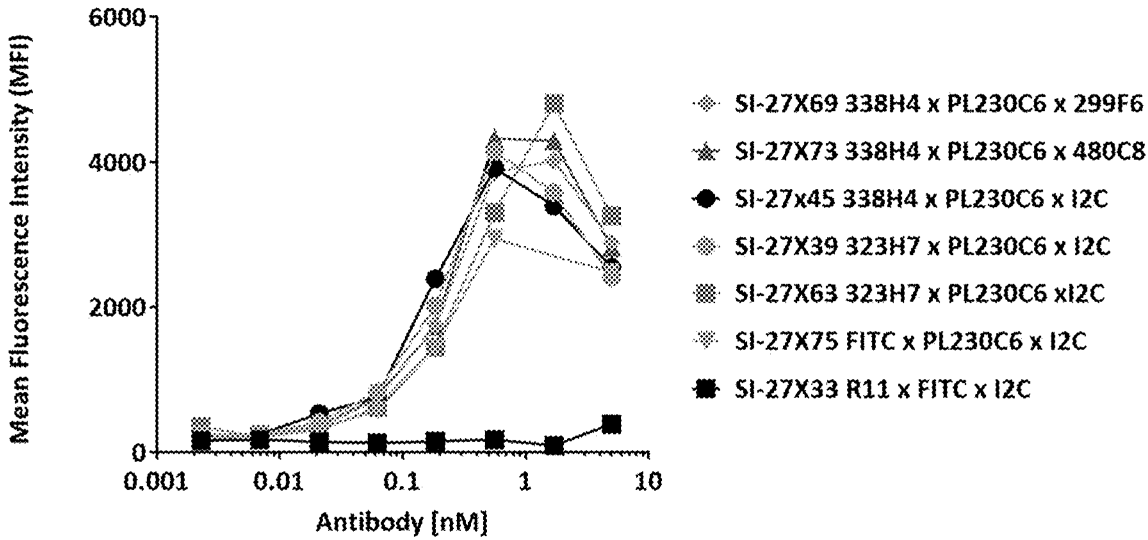

FIGURE 6 is a snapshot of experiment results showing re-directed T cell cytotoxicity assay with CD3+ T cells as effectors and ROR1 positive B-Acute Lymphoblastic Leukemia cell line Kasumi-2 as targets according to some embodiments.
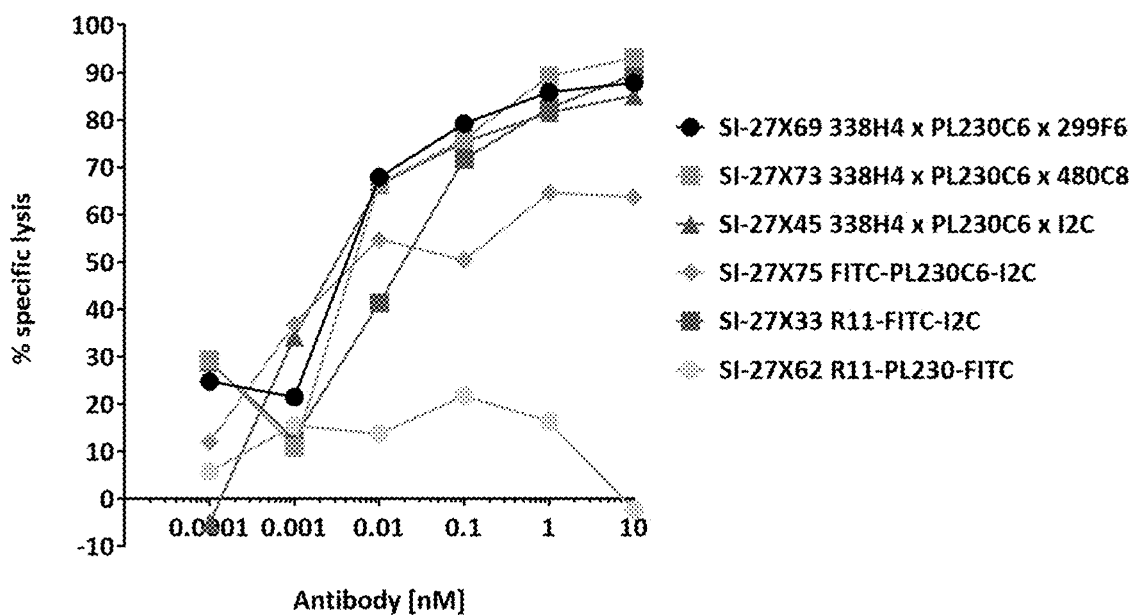

FIGURE 7 is a snapshot of experiment results showing re-directed T cell cytotoxicity assay with CD4+ T regulatory cells as effectors and ROR1 positive B-Acute Lymphoblastic Leukemia cell line Kasumi-2 as targets according to some embodiments.
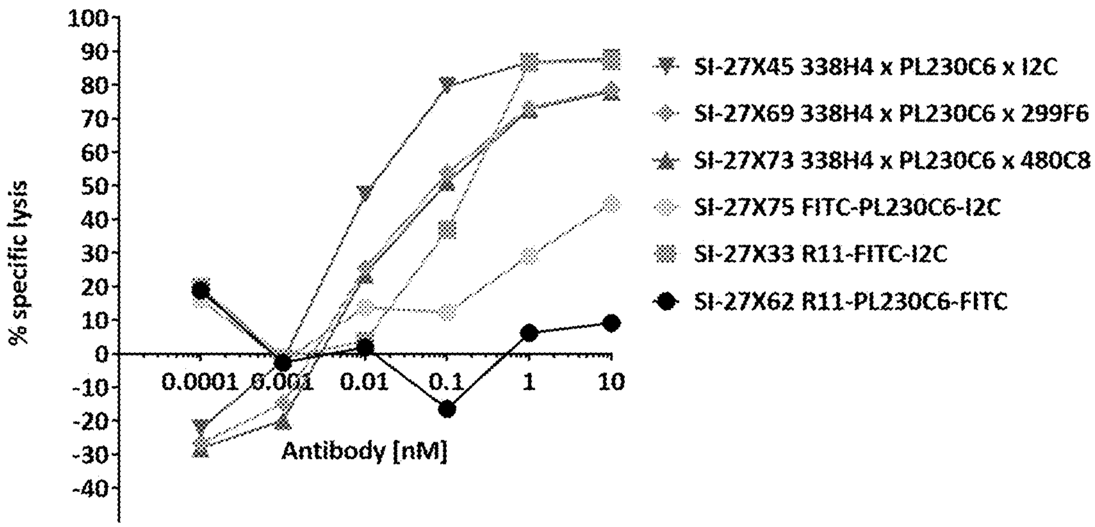

FIGURE 8 is a snapshot of experiment results showing re-directed T cell cytotoxicity assay with "exhausted" CD8+ T cells as effectors and ROR1 positive B-Acute Lymphoblastic Leukemia cell line Kasumi-2 as targets according to some embodiments.
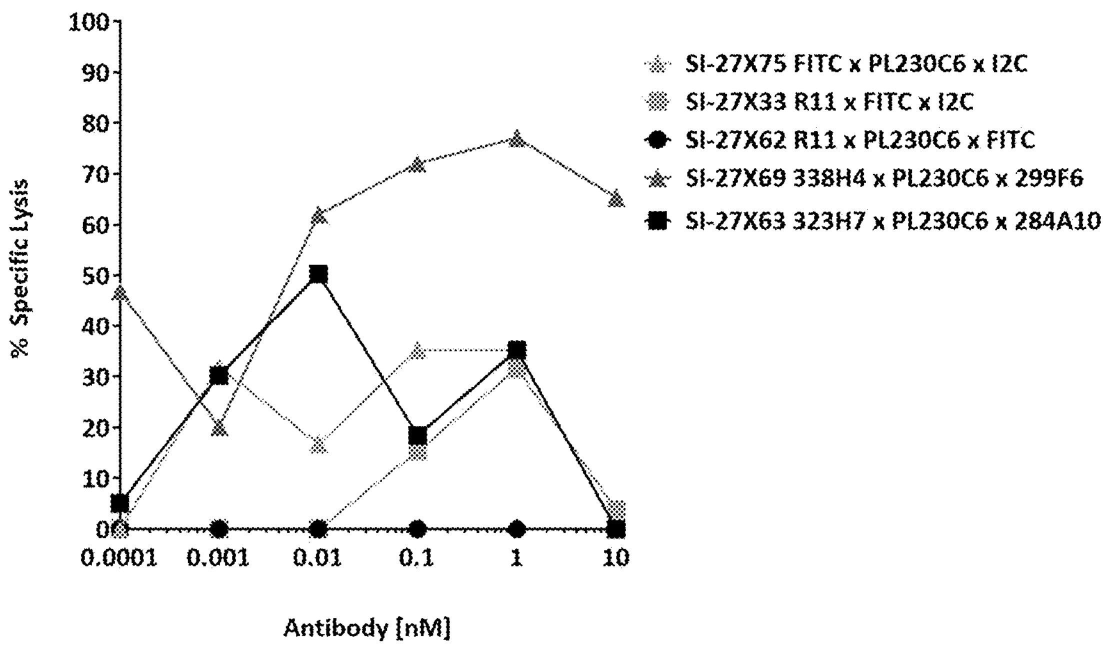

FIGURE 9 is a snapshot of experiment results showing re-directed T cell cytotoxicity assay with peripheral blood mononuclear cells as effectors and the glioblastoma cell line U87-EGFRviii as targets according to some embodiments.
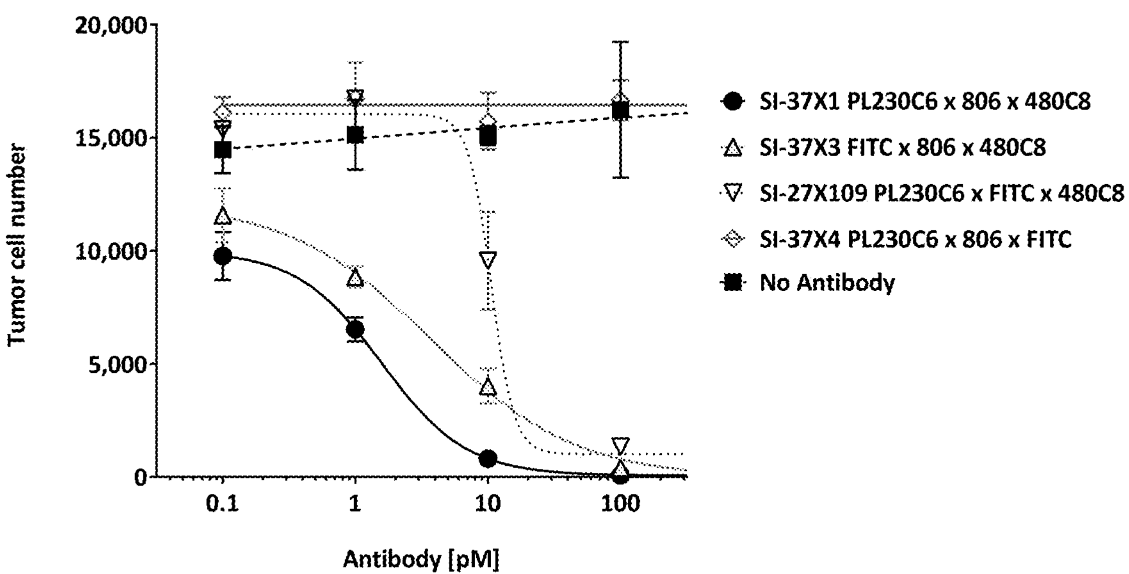

FIGURE 10 is a snapshot of experiment results showing re-directed T cell cytotoxicity assay with peripheral blood mononuclear cells as effectors and the glioblastoma cell line U87-EGFRviii as targets according to some embodiments.
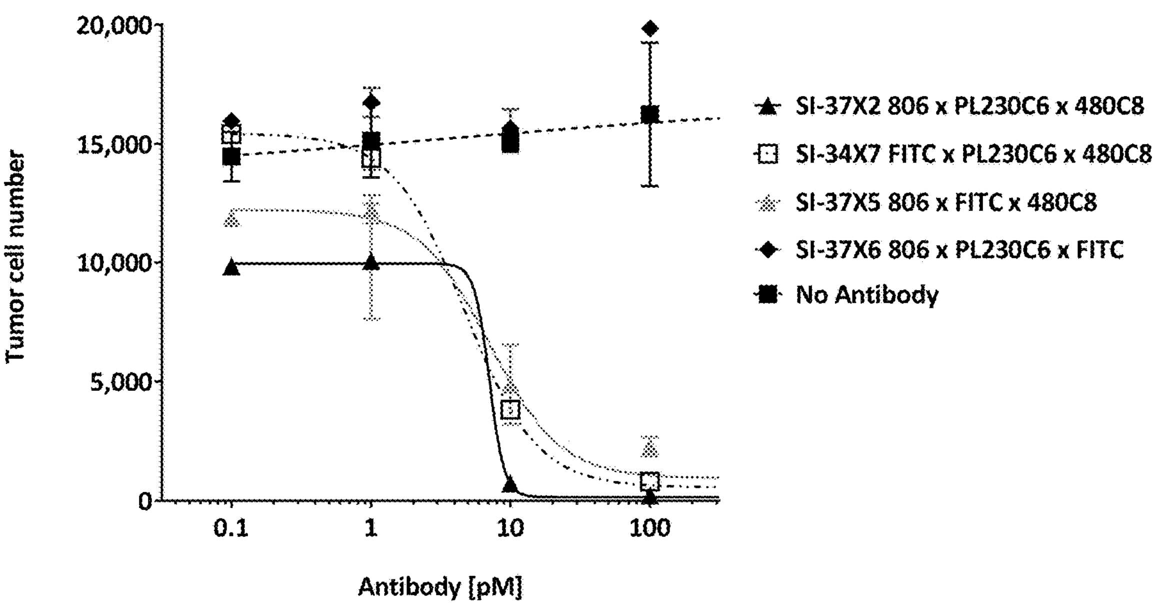

FIGURE 11 is a snapshot of experiment results showing re-directed T cell cytotoxicity assay with PBMC cells as effectors and CD19 positive B-Acute Lymphoblastic Leukemia cell line Kasumi-2 as targets according to some embodiments.
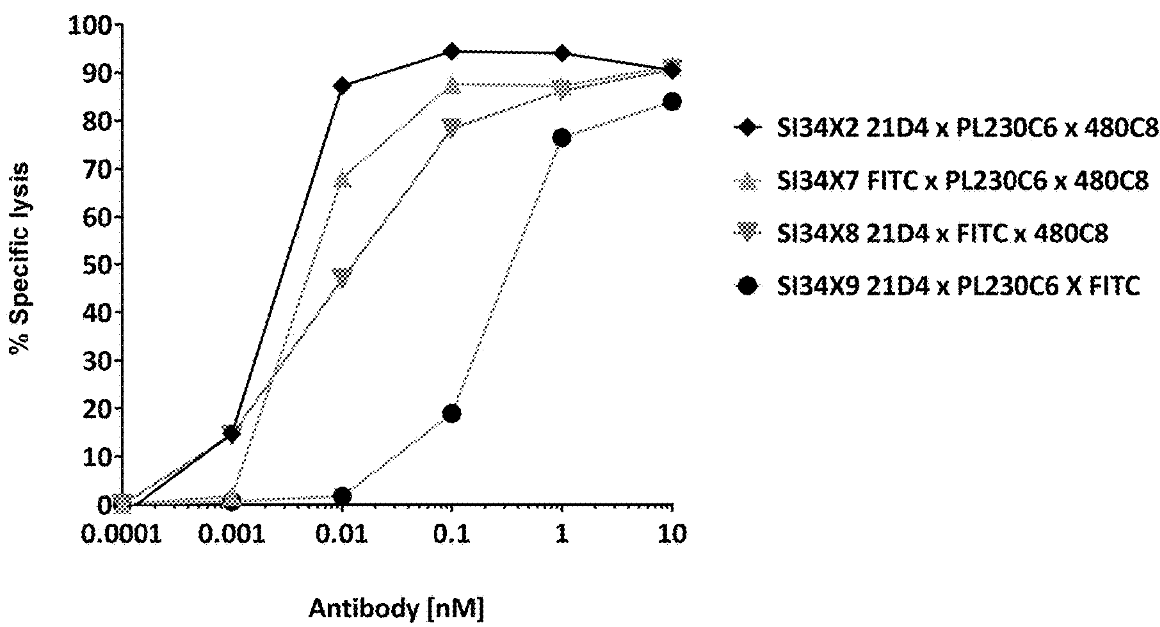

MULTI-SPECIFIC ANTIBODIES AND METHODS OF USING THEREOF

CROSS REFERENCE TO RELATED APPLICATIONS

This application is a division of U.S. application Ser. No. 16/615,117, filed Nov. 19, 2019, and claims the benefit of U.S. Provisional Patent Application No. 62/524,554, filed Jun. 25, 2017, both of which are expressly incorporated herein by reference in their entirety.

TECHNICAL FIELD

The present disclosure generally relates to the technical field of biologic therapeutics, and more particularly relates to making and using multi-specific antibodies.

BACKGROUND

Cancer cells develop various strategies to evade destruction and elimination by the immune system of the host. One main mechanism is immune-editing where the immune response against the original cancer provides immunological pressure to select for variants of the original cancer cell that are not recognized by the immune system through the down-regulation of the Major Histocompatibility Complex (MHC) presentation of tumour specific antigens. Another mechanism resides within the tumour microenvironment where cells such as T regulatory cells (Treg) or Myeloid-derived suppressor cells (M DSC) actively inhibit the cytolytic activity of cytotoxic T cells or natural killer cells through the production of immune-suppressive cytokines such as Transforming Growth Factor Beta (TGF▯) or Interleukin-10 (IL-10). Also, within the tumour microenvironment cancer cells often express one or more "Immune Checkpoint" receptors or molecules such as Programmed Death Ligand 1 (PD-L1) that bind to inhibitory receptors on T cells such as Programmed cell death protein 1 (PD-1) that plays an important role in down-regulating the immune response and promoting self-tolerance. [Vinay et al., 2015, Semin, Cancer Biol., (35): 5185-S198, Dunn et al., 2004, Immunity, 21(2): 137-48; Adachi & Tamada, 2015, Cancer Sci., 106(8): 945-50].

As the mechanisms by which tumours evade recognition by the immune system continue to be better understood new treatment modalities that target these mechanisms have recently emerged. On Mar. 25, 2011, the U. S. Food and Drug Administration (FDA) approved ipilimumab injection (Yervoy, Bristol-Myers Squibb) for the treatment of unresectable or metastatic melanoma. Yervoy binds to cytotoxic T-lymphocyte-associated protein 4 (CTLA-4) expressed on activated T cells and blocks the interaction of CTLA-4 with CD80/86 on antigen-presenting cells thereby blocking the negative or inhibitory signal delivered into the T cell through CTLA-4 resulting in re-activation of the antigen-specific T cell leading to, in many patients, eradication of the tumour. A few years later in 2014 the FDA approved Keytruda (Pembrolizumab, Merck) and Opdivo (Nivolumab, Bristol-Myers Squibb) for treatment of advanced melanoma. These monoclonal antibodies bind to PD-1 which is expressed on activated and/or exhausted T cells and block the interaction of PD-1 with PD-L1 expressed on tumours thereby eliminating the inhibitory signal through PD-1 into the T cell resulting in re-activation of the antigen-specific T cell leading to again, in many patients, eradication of the tumour. Since then additional clinical trials have been performed comparing the single monoclonal antibody Yervoy to the combination of the monoclonal antibodies Yervoy and Opdivo in the treatment of advanced melanoma which showed improvement in overall survival and progression-free survival in the patients treated with the combination of antibodies. (Hodi et al., 2016*, Lancet Oncol.* 17(11):1558-1568, Hellman et al., 2018, Cancer Cell 33(5):853-861). However, as many clinical trials have shown a great benefit of treating cancer patients with monoclonal antibodies that are specific for one or more immune checkpoint molecules data has emerged that only those patients with a high mutational burden that generates a novel T cell epitope(s) which is recognized by antigen-specific T cells show a clinical response (Snyder et al., 2014, NEJM 371:2189-2199). Those patients that have a low tumour mutational load mostly do not show an objective clinical response (Snyder et al., 2014, NEJM 371:2189-2199, Hellman et al., 2018, Cancer Cell 33(5):853-861).

In recent years other groups have developed an alternate approach that does not require the presence of neoepitope presentation by antigen-presenting cells to activate T cells. One example is the development of a bi-specific antibody where the binding domain of an antibody which is specific for a tumour associated antigen, e.g., CD19, is linked to an antibody binding domain specific for CD3 on T cells thus creating a bi-specific T cell engager or BiTe molecule. In 2014, the FDA approved a bi-specific antibody called Blinotumumab for the treatment of Precursor B-Cell Acute Lymphoblastic Leukemia. Blinotumumab links the scFv specific for CD19 expressed on leukemic cells with the scFv specific for CD3 expressed on T cells (Bejnjamin and Stein 2016, Ther Adv Hematol 7(3):142-146). However, despite an initial response rate of >50% in patients with relapsed or refractory ALL many patients are resistant to blinotumumab therapy or relapse after successful treatment with blinotumumab. Evidence is emerging that the resistance to blinotumumab or the relapse after blinotumumab treatment is attributable to the expression of immune checkpoint inhibitory molecules expressed on tumour cells such as PD-L1 that drives an inhibitory signal through PD-1 expressed on activated T cells (Feucht et al., 2016, Oncotarget 7(47):76902-76919). In a case study of a patient who was resistant to therapy with blinotumumab a second round of blinotumumab therapy was performed but with the addition of a monoclonal antibody, pembrolizumab (Keytruda, Merck), which is specific for PD-1 and blocks the interaction of T cell-expressed PD-1 with tumour cell expressed PD-L1 resulted in a dramatic response and reduction of tumour cells in the bone marrow from 45% to less than 5% in this one patient (Feucht et al., 2016, Oncotarget 7(47):76902-76919). These results show that combining a bi-specific BiTe molecule with one or more monoclonal antibodies can significantly increase clinical activity compared to either agent alone.

SUMMARY

In one aspect, the application provides tri-specific antibody monomers, the antigen-binding fragments thereof, and multi-specific antibodies.

In one embodiment, the tri-specific antibody monomer having a N-terminal and a C-terminal, comprising in tandem from the N-terminal to the C-terminal, a first scFv domain at the N-terminal, a Fab domain, a Fc domain, and a second scFv domain at the C-terminal. The first scFv domain, the Fab domain, and the second scFv domain each has a binding specificity against a different antigen.

The antigen may be a tumour antigen, an immune signaling antigen, or a combination thereof. In one embodiment, the first scFv domain, the Fab domain, and the second scFv domain each has a binding specificity against a tumour antigen. In one embodiment, the first scFv domain, the Fab domain, and the second scFv domain each has a binding specificity against an immune signaling antigen.

In one embodiment, the first scFv domain has a binding specificity against a tumour antigen. In one embodiment, the first scFv domain has a binding specificity against an immune signaling antigen. In one embodiment, the Fab domain has a binding specificity against a tumour antigen. In one embodiment, the Fab domain has a binding specificity against an immune signaling antigen. In one embodiment, the second scFv domain has a binding specificity against a tumour antigen. In one embodiment, the second scFv domain has a binding specificity against an immune signaling antigen.

In one embodiment, the first scFv domain, the Fab domain, and the second scFv domain each independently has a binding specificity against an antigen selected from ROR1, PD-L1, CD3, CD28, 41BB, CEA, HER2, EGFRvIII, EGFR, LMP1, LMP2A, Mesothelin, PSMA, EpCAM, glypican-3, gpA33, GD2, TROP2, NKG2D, BCMA, CD19, CD20, CD33, CD123, CD22, CD30, PDL1, PD1, OX40, 4-1BB, GITR, TIGIT, TIM-3, LAG-3, CTLA4, CD40, VISTA, ICOS, BTLA, LIGHT, HVEM, CSF1R, CD73, and CD39.

In one embodiment, the first scFv domain, the Fab domain, and the second scFv domain each independently has a binding specificity against an antigen selected from ROR1, PD-L1, and CD3. In one embodiment, the first scFv domain has a binding specificity against ROR1. In one embodiment, the Fab domain has a binding specificity against PD-L1. In one embodiment, the second scFv domain has a binding specificity against CD3. In one embodiment, the first scFv domain has a binding specificity against ROR1, the Fab domain has a binding specificity against PD-L1, and the second scFv has a binding specificity against CD3.

The antibody monomers and the antibodies disclosed herein may be humanized. In one embodiment, the Fc domain is a human IgG1 Fc.

The application provides scFv domains for the tri-specific antibody monomer and antibodies disclosed herein. In one embodiment, the scFv domain includes an amino acid sequence having a percentage homology to SEQ ID NO: 13-34, 39-46. The percentage homology is not less than 70%, 80%, 90%, 95%. 98%, or 99%.

The application provides Fab domains for the tri-specific antibody monomers and antibodies disclosed herein. In one embodiment, the Fab domain includes an amino acid sequence having a percentage homology to SEQ ID NO: 13-16. The percentage homology is not less than 70%, 80%, 90%, 95%. 98%, or 99%.

The application provides Fc domains for the tri-specific antibody monomers and antibodies disclosed herein. In one embodiment, the Fab domain includes an amino acid sequence having a percentage homology to SEQ ID Nos: 47 and 48. The percentage homology is not less than 70%, 80%, 90%, 95%. 98%, or 99%.

The first scFv domain, the second scFv domain, the Fab domain and the Fc domain in the tri-specific antibody monomers and antibodies may be any combination of sequences disclosed herein.

In one embodiment, the application provides a multi-specific antibody, comprising a tri-specific antibody monomer. In one embodiment, the multi-specific antibody includes a first tri-specific monomer and a second tri-specific monomer. In one embodiment, the first and the second tri-specific monomers are the same and the multi-specific antibody is a symmetric tri-specific antibody. In one embodiment, the first and the second tri-specific monomers are different and the multi-specific antibody is an asymmetric antibody. In one embodiment, the multi-specific antibody is a tri-specific antibody, a tetra-specific antibody, a penta-specific antibody, or a hexa-specific antibody.

In one embodiment, the multi-specific antibody includes a first tri-specific antibody monomer and a second tri-specific antibody monomer. The first tri-specific antibody monomer has a N-terminal and a C-terminal and includes, in tandem from the N-terminal to the C-terminal, a first scFv domain at the N-terminal, a first Fab domain, a first Fc domain, and a second scFv domain at the C-terminal. The second multi-specific antibody monomer has a N-terminal and a C-terminal and includes, in tandem from the N-terminal to the C-terminal, a third scFv domain at the N-terminal, a second Fab domain, a second Fc domain, and a fourth scFv domain at the C-terminal. In one embodiment, the third scFv domain, a second Fab domain and a fourth scFv domain each has a binding specificity against a different antigen.

In one embodiment, the second scFv domain and the fourth scFv domain each has a binding specificity against a different antigen. In one embodiment, the first scFv domain and the third scFv domain each has a binding specificity against a different antigen. In one embodiment, the first Fab domain and the second Fab domain each has a binding specificity against a different antigen.

In one embodiment, the multi-specific antibody is a tri-specific antibody. In one embodiment, the application provides an engineered antibody with 3 different binding domains or a "tri-specific" antibody. One binding domain is specific for CD3 on T cells, a second binding domain is specific for a tumour associated antigen including but not limited to ROR1, CEA, HER2, EGFR, EGFRvIII, LMP1, LMP2A, Mesothelin, PSMA, EpCAM, glypican-3, gpA33, GD2, TROP2, BCMA, CD19, CD20, CD33, CD123, CD22, CD30, and a third binding domain which is specific for an immune checkpoint modulator such as PDL1, PD1, OX40, 4-1BB, GITR, TIGIT, TIM-3, LAG-3, CTLA4, CD40, VISTA, ICOS, BTLA, Light, HVEM, CD73, CD39, etc. In one embodiment, the tri-specific antibody includes an amino acid sequence having a percentage homology to SEQ ID NO as disclosed in this application. The percentage homology is not less than 70%, 80%, 90%, 95%. 98%, or 99%.

In one embodiment, the antibody is purified, isolated, or non-natural existing.

The application further provides the isolated nucleic acid sequence encoding the tri-specific monomers, the antigen-binding fragments thereof, or the multi-specific antibodies disclosed herein. In one embodiment, the isolated nucleic acid sequence encodes the tri-specific antibody monomer disclosed herein.

The application further provides expression vector or host cells including the isolated nucleic acid sequence disclosed herein. In one embodiment, the host cell includes the expression vector. In one embodiment, the host cell is a prokaryotic cell or a eukaryotic cell.

The application further provides immuno-conjugates including a cytotoxic agent or an imaging agent linked to the tri-specific antibody monomers, the antigen-binding fragments, or the multi-specific antibodies through a linker.

The linker may be cleavable or non-cleavable. In one embodiment, the linker may be a covalent bond such as an ester bond, an ether bond, an amid bond, a disulphide bond, an imide bond, a sulfone bond, a phosphate bond, a phosphorus ester bond, a peptide bond, or a combination thereof. In one embodiment, the linker may include a hydrophobic poly(ethylene glycol) linker.

The cytotoxic agent may include a chemotherapeutic agent, a growth inhibitory agent, a cytotoxic agent from class of calicheamicin, an antimitotic agent, a toxin, a radioactive isotope, a therapeutic agent, or a combination thereof. In one embodiment, the cytotoxic agent may include a calicheamicin, ozogamicin, monomethyl auristatin E, emtansine, a derivative or a combination thereof.

The imaging agent may be any compound useful for imaging purpose. In one embodiment, the imaging agent may be radionuclide, a florescent agent, a quantum dots, or a combination thereof.

In another aspect, the application provides methods of making the antibody monomers, their antigen-binding fragments, or antibodies disclosed herein. In one embodiment, the method for producing a multi-specific antibody includes the steps of culturing a host cell containing the nucleic acid sequences encoding the antibodies so that the DNA sequence encoding the antibody is expressed and purifying said antibody.

In a further aspect, the application provides pharmaceutical compositions. In one embodiment, the pharmaceutical composition includes a pharmaceutically acceptable carrier and the tri-specific antibody monomers, the multi-specific antibodies, the immuno-conjugate, or a combination thereof.

In one embodiment, the pharmaceutical composition further includes a therapeutic agent. The therapeutic agent may include a radioisotope, radionuclide, a toxin, a chemotherapeutic agent, an antibody, an enzyme, or a combination thereof. In one embodiment, the therapeutic agent comprises an anti-estrogen agent, a receptor tyrosine kinase inhibitor, a kinase inhibitor, a cell cycle inhibitor, a DNA, RNA or protein synthesis inhibitor, a RAS inhibitor, an immune check point inhibitor, or a combination thereof.

In a further aspect, the application provides methods for treating or preventing a cancer using the tri-specific antibody monomers, the multi-specific antibodies, the immuno-conjugate, or a combination thereof. In one embodiment, the method includes administering an effective amount of the tri-specific antibody monomers, the multi-specific antibodies, the immuno-conjugate, or a combination thereof to a subject in need of such treatment. In one embodiment, the method includes administering to a subject in need of such treatment an effective amount of a pharmaceutical composition comprising the tri-specific antibody monomers, the multi-specific antibodies, the immuno-conjugate, or a combination thereof. In one embodiment, the method of treating a subject with a cancer includes administering to the subject an effective amount of the tri-specific antibody disclosed herein.

In one embodiment, the method includes directly injecting into the tumour site an effective amount of multi-specific monomers, multi-specific antibodies, the immuno-conjugates, the antigen-binding fragment thereof.

In some embodiments, the advantages that the disclosed methods of treatment have over currently existing therapies include, without limitation: 1) Inclusion of an IgG Fc domain will confer the characteristic of a longer half-life in serum compared to a bi-specific BiTe molecule, 2) Inclusion of a binding domain which is specific for an immune checkpoint modulator e.g., PD-L1, may inhibit the suppressive effect of tumour expressed PD-L1 binding to PD-1 expressed on an activated T cell, and 3) Cross-link CD3 on T cells with tumour associated antigens thus “re-directing” T cells to kill the tumour without the need to remove T cells from the patient and genetically modify them to be specific for the tumour cell before re-introducing them back into the patient as done for chimeric antigen receptor T cells (CAR-T).

Varieties of cancer may be treated with the tri-specific antibody monomers, the multi-specific antibodies, the immuno-conjugate, or a combination thereof. Example cancers include without limitation breast cancer, colorectal cancer, anal cancer, pancreatic cancer, gallbladder cancer, bile duct cancer, head and neck cancer, nasopharyngeal cancer, skin cancer, melanoma, ovarian cancer, prostate cancer, urethral cancer, lung cancer, non-small lung cell cancer, small cell lung cancer, brain tumour, glioma, neuroblastoma, esophageal cancer, gastric cancer, liver cancer, kidney cancer, bladder cancer, cervical cancer, endometrial cancer, thyroid cancer, eye cancer, sarcoma, bone cancer, leukemia, myeloma or lymphoma. In one embodiment, the cancer comprises cells expressing ROR1, CEA, HER2, EGFR, EGFRvIII, LMP1, LMP2A, Mesothelin, PSMA, EpCAM, glypican-3, gpA33, GD2, TROP2, NKG2D, BCMA, CD19, CD20, CD33, CD123, CD22, CD30.

The method of treating a subject may include co-administering an effective amount of a therapeutic agent. In one embodiment, the therapeutic agent comprises an antibody, a chemotherapy agent, an enzyme, or a combination thereof. In one embodiment, the therapeutic agent comprises an anti-estrogen agent, a receptor tyrosine kinase inhibitor, a kinase inhibitor, a cell cycle inhibitor, a DNA, RNA or protein synthesis inhibitor, a RAS inhibitor, or a combination thereof.

In one embodiment, the therapeutic agent comprises capecitabine, cisplatin, Cyclophosphamide, methotrexate, 5-fluorouracil, Doxorubicin, cyclophosphamide, Mustine, vincristine, procarbazine, prednisolone, bleomycin, vinblastine, dacarbazine, etoposide, Epirubicin, pemetrexed, folinic acid, gemicitabine, oxaliplatin, irinotecan, topotecan, camptothecin, docetaxel, paclitaxel, fulvestrant, tamoxifen, letrozole, exemestane, anastrozole, aminoglutethimide, testolactone, vorozole, formestane, fadrozole, erlotinib, lafatinib, dasatinib, gefitinib, osimertinib, vandertanib, afatinib, imatinib, pazopinib, lapatinib, sunitinib, nilotinib, sorafenib, nab-palitaxel, Everolimus, temsirolimus, Dabrafenib, vemurafenib, trametinib, vintafolide, apatinib, crizotinib, periforsine, olaparib, Bortezomib, tofacitinib, trastuzumab, a derivative or a combination thereof.

In one embodiment, the therapeutic agent comprises a check point inhibitor. In one embodiment, the therapeutic agent comprises an inhibitor of PD1, PDL1, CTLA4, 4-1BB, OX40, GITR, ICOS, LIGHT, TIM3, LAG3, TIGIT, CD40, CD27, HVEM, BTLA, VISTA, B7H4, CSF1R, NKG2D, CD73, a derivative or a combination thereof.

The subject be treated may be a human. In one embodiment, the application provides a solution comprising an effective concentration of the tri-specific antibody monomers, the antigen-binding fragments thereof, the multi-specific antibodies, of a combination thereof, and the solution is blood plasma in a subject.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE DRAWINGS AND TABLES

The foregoing and other features of this disclosure will become more fully apparent from the following description and appended claims, taken in conjunction with the accompanying drawings. Understanding that these drawings depict only several embodiments arranged in accordance with the disclosure and are, therefore, not to be considered limiting of its scope, the disclosure will be described with additional specificity and detail through use of the accompanying drawings, in which:

FIG. 1 shows the example tri-specific antibodies used in binding and RTCC assays.

FIG. 2 shows the specificity of the antibody binding domains used in the example tri-specific antibodies.

FIG. 3 is a diagram showing a symmetric tri-specific antibody according to at least one embodiment.

FIG. 4 is a snapshot of experiment results showing FACS analysis of tri-specific antibodies binding to ROR1 expressing CHO cells according to some embodiments.

FIG. 5 is a snapshot of experiment results showing FACS analysis of tri-specific antibody binding to PD-L1 expressing CHO cells according to some embodiments.

FIG. 6 is a snapshot of experiment results showing re-directed T cell cytotoxicity assay with CD3+ T cells as effectors and ROR1 positive B-Acute Lymphoblastic Leukemia cell line Kasumi-2 as targets according to some embodiments.

FIG. 7 is a snapshot of experiment results showing re-directed T cell cytotoxicity assay with CD4+T regulatory cells as effectors and ROR1 positive B-Acute Lymphoblastic Leukemia cell line Kasumi-2 as targets according to some embodiments.

FIG. 8 is a snapshot of experiment results showing re-directed T cell cytotoxicity assay with "exhausted" CD8+ T cells as effectors and ROR1 positive B-Acute Lymphoblastic Leukemia cell line Kasumi-2 as targets according to some embodiments.

FIG. 9 is a snapshot of experiment results showing re-directed T cell cytotoxicity assay with peripheral blood mononuclear cells as effectors and the glioblastoma cell line U87-EGFRviii as targets according to some embodiments.

FIG. 10 is a snapshot of experiment results showing re-directed T cell cytotoxicity assay with peripheral blood mononuclear cells as effectors and the glioblastoma cell line U87-EGFRviii as targets according to some embodiments.

FIG. 11 is a snapshot of experiment results showing re-directed T cell cytotoxicity assay with PBMC cells as effectors and CD19 positive B-Acute Lymphoblastic Leukemia cell line Kasumi-2 as targets according to some embodiments.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The disclosure provides, among others, isolated antibodies, methods of making such antibodies, bispecific or multi-specific molecules, antibody-drug conjugates and/or immuno-conjugates composed from such antibodies or antigen binding fragments, pharmaceutical compositions containing the antibodies, bispecific or multi-specific molecules, antibody-drug conjugates and/or immuno-conjugates, the methods for making the molecules and compositions, and the methods for treating cancer using the molecules and compositions disclosed herein.

The term "antibody" is used in the broadest sense and specifically covers single monoclonal antibodies (including agonist and antagonist antibodies), antibody compositions with polyepitopic specificity, as well as antibody fragments (e.g., Fab, $F(ab')_2$, and Fv), so long as they exhibit the desired biological activity. In some embodiments, the antibody may be monoclonal, polyclonal, chimeric, single chain, bispecific or bi-effective, simianized, human and humanized antibodies as well as active fragments thereof. Examples of active fragments of molecules that bind to known antigens include Fab, $F(ab')_2$, scFv and Fv fragments, including the products of an Fab immunoglobulin expression library and epitope-binding fragments of any of the antibodies and fragments mentioned above. In some embodiments, antibody may include immunoglobulin molecules and immunologically active portions of immunoglobulin molecules, i.e. molecules that contain a binding site that immunospecifically bind an antigen. The immunoglobulin can be of any type (IgG, IgM, IgD, IgE, IgA and IgY) or class (IgG1, IgG2, IgG3, IgG4, IgA1 and IgA2) or subclasses of immunoglobulin molecule. In one embodiment, the antibody may be whole antibodies and any antigen-binding fragment derived from the whole antibodies. A typical antibody refers to heterotetrameric protein comprising typically of two heavy (H) chains and two light (L) chains. Each heavy chain is comprised of a heavy chain variable domain (abbreviated as VH) and a heavy chain constant domain. Each light chain is comprised of a light chain variable domain (abbreviated as VL) and a light chain constant domain. The VH and VL regions can be further subdivided into domains of hypervariable complementarity determining regions (CDR), and more conserved regions called framework regions (FR). Each variable domain (either VH or VL) is typically composed of three CDRs and four FRs, arranged in the following order: FR1, CDR1, FR2, CDR2, FR3, CDR3, FR4 from amino-terminus to carboxy-terminus. Within the variable regions of the light and heavy chains there are binding regions that interacts with the antigen.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler & Milstein, Nature, 256:495 (1975), or may be made by recombinant DNA methods (see, e.g., U.S. Pat. No. 4,816,567).

The monoclonal antibodies may include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA,* 81:6851-6855 [1984]).

Monoclonal antibodies can be produced using various methods including mouse hybridoma or phage display (see Siegel. Transfus. Clin. Biol. 9:15-22 (2002) for a review) or from molecular cloning of antibodies directly from primary B cells (see Tiller. New Biotechnol. 28:453-7 (2011)). In the present disclosure antibodies were created by the immunization of rabbits with both human PD-L1 protein and cells transiently expressing human PD-L1 on the cell surface. Rabbits are known to create antibodies of high affinity, diversity and specificity (Weber et al. Exp. Mol. Med. 49:e305). B cells from immunized animals were cultured in vitro and screened for the production of anti-PD-L1 antibodies. The antibody variable genes were isolated using recombinant DNA techniques and the resulting antibodies were expressed recombinantly and further screened for desired features such as ability to inhibit the binding of PD-L1 to PD-1, the ability to bind to non-human primate PD-L1 and the ability to enhance human T-cell activation. This general method of antibody discovery is similar to that described in Seeber et al. PLOS One. 9:e86184 (2014).

The term "antigen- or epitope-binding portion or fragment" refers to fragments of an antibody that are capable of binding to an antigen (PD-L1 in this case). These fragments may be capable of the antigen-binding function and additional functions of the intact antibody. Examples of binding fragments include, but are not limited to a single-chain Fv fragment (scFv) consisting of the VL and VH domains of a single arm of an antibody connected in a single polypeptide chain by a synthetic linker or a Fab fragment which is a monovalent fragment consisting of the VL, constant light (CL), VH and constant heavy 1 (CH1) domains. Antibody fragments can be even smaller sub-fragments and can consist of domains as small as a single CDR domain, in particular the CDR3 regions from either the VL and/or VH domains (for example see Beiboer et al., J. Mol. Biol. 296:833-49 (2000)). Antibody fragments are produced using conventional methods known to those skilled in the art. The antibody fragments are can be screened for utility using the same techniques employed with intact antibodies.

The "antigen- or epitope-binding fragments" can be derived from an antibody of the present disclosure by a number of art-known techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

Papain digestion of antibodies produces two identical antigen binding fragments, called "Fab" fragments, each with a single antigen binding site, and a residual "Fc" fragment, whose name reflects its ability to crystallize readily. Pepsin treatment yields an $F(ab')_2$ fragment that has two antigen combining sites and is still capable of cross-linking antigen.

The Fab fragment may contain the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other, chemical couplings of antibody fragments are also known.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the VH-VL dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The "light chains" of antibodies (immunoglobulins) from any vertebrate species can be assigned to one of two clearly distinct types, called kappa and lambda (Λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called α, delta, epsilon, γ, and μ, respectively. The subunit structures and three-dimensional configurations of different classes of immunoglobulins are well known.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity. Methods to obtain "humanized antibodies" are well known to those skilled in the art. (see, e.g., Queen et al., Proc. Natl Acad Sci USA, 86:10029-10032 (1989), Hodgson et al., Bio/Technology, 9:421 (1991)).

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

By "isolated" is meant a biological molecule free from at least some of the components with which it naturally occurs. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic a binding specificity.

"Recombinant" means the antibodies are generated using recombinant nucleic acid techniques in exogeneous host cells.

The term "antigen" refers to an entity or fragment thereof which can induce an immune response in an organism, particularly an animal, more particularly a mammal including a human. The term includes immunogens and regions thereof responsible for antigenicity or antigenic determinants.

Also as used herein, the term "immunogenic" refers to substances which elicit or enhance the production of antibodies, T-cells or other reactive immune cells directed against an immunogenic agent and contribute to an immune response in humans or animals. An immune response occurs when an individual produces sufficient antibodies, T-cells and other reactive immune cells against administered immunogenic compositions of the present disclosure to moderate or alleviate the disorder to be treated.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs. The deviations appearing in the comparison between a given sequence and the above-described sequences of the disclosure may be caused for instance by addition, deletion, substitution, insertion or recombination.

In one aspect, the application provides tri-specific antibody monomers, antigen-binding fragments thereof, and the multi-specific antibodies. In some embodiments, the application describes the generation of symmetric tri-specific antibodies and antigen-binding fragments thereof. In one embodiment, the tri-specific antibody is a dimer of a monomer having 3 different antibody binding domains.

The monomer has an N-terminal single-chain fragment variable (scFv) with one binding specificity, followed by the fragment antibody (Fab) domain with a second binding specificity, followed by a human IgG1 CH1, hinge, CH2, and CH3 domains, followed by an scFv with a third binding specificity at the C-terminal.

The corresponding kappa or lambda light chain is expressed as a separate VL-CL chain as with a typical antibody. The monomer has one domain binding to a tumour associated antigen, one domain binding to an immune checkpoint domain with either agonist or antagonist characteristics, and one domain binding to the CD3 complex on T cells, as shown in FIG. 3.

In one embodiment, N-terminal scFv are oriented VL-VH, operably linked by a 20 amino acid G4S linker and C-terminal scFv are oriented VH-VL, linked by either a 15 or 20 amino acid G4S linker. Each of these linkers genetically fuses the C-terminus of one domain to the N-terminus of its partner domain. N-terminal scFv are fused to the Fab domain with a shorter, 10 amino acid G4S linker. Likewise, the C-terminal scFv are fused to the end of the human IgG1 Fc domain with a 10 amino acid G4S linker.

In one embodiment, the symmetric tri-specific antibodies were designed to bind a tumour associated antigen (TAA) such a sROR1 (Karvonen et al, 2017, Biochem Soc Trans, 45(2): 457-464; Aghebati-Maleki et al, 2017, Biomed Pharmacother. 88:814-822; Shabani et al, 2015, Expert Opin Ther Targets. 19(7):941-55.) or CD19 (Johnsen et al., 2014 Leuk Lymphoma, 55(6):1251-60) or the viii mutant of the epidermal growth factor receptor (Gan et al., 2013, FEBS J. 280(21):5350-70).

In one embodiment, the tri-specific antibodies were designed to bind to a second antigen involved in the immune response against cancer cells such as PD-L1 which is expressed on many tumours in the tumour microenvironment (Dunn & Rao, 2017, Mol Immunol. 13; 87:227-239; Balar & Weber. 2017, Cancer Immunol Immunother. 66(5): 551-564.).

In one embodiment, the tri-specific antibodies were also designed to bind to a third antigen, CD3, which is T-cell specific. Antibodies of this class can bind to the tumour through the TAA and/or PD-L1 while engaging any CD3+ T-cells in the vicinity of the tumour through CD3, a process referred to as re-directed T-cell cytotoxicity or RTCC (Baeuerle and Reinhardt, 2009, Cancer res. 69(12):4941-4).

Cytotoxicity is generally achieved through the actions of CD8+ T-cells although a role for CD4+ T-cells has been demonstrated (Haas et al., 2009 Immunobiology, 214(6): 441-53). In addition, the PD-L1 binding domain used in these tri-specific antibodies has been selected to block the interaction of PD-1 on T cells with PD-L1 expressed on the tumour cells thus reducing or eliminating this inhibitory pathway to T cell activation (Feucht et al., 2016, Oncotarget 7(47):76902-76919).

To eliminate cross-linking of tri-specific antibodies on the surface of cells expressing Fc-receptors, amino acid mutations (alanine) near the IgG1 hinge region were introduced at positions L234, L235, and G237 (Stroh) W R, 2009, Curr Opin Biotechnol. 20(6):685-91) resulting in an Fc domain without antibody-dependent cellular cytotoxicity (ADCC) or complement-dependent cytotoxicity (CDC) effector function referred to as an "effector null" phenotype.

In one embodiment, the tri-specific molecules target either human ROR1 (SEQIDs 5-8), human CD19 (SEQIDs 43-46) or EGFR vIII (SEQIDs 39-42) as tumour associated antigens. Each of these targeted tri-specific proteins also carries an anti-human PD-L1 (SEQIDs 13-16) and anti-human CD3 binding domain (SEQIDs 21-24). These binding domains were converted to scFv, VLVH, for placement at the N-terminal Domain 1 (D1) or scFv, VHVL, for placement at the C-terminal Domain 3 (D3) of the peptide.

In one embodiment, the scFv molecules described herein contain a 20 amino acid flexible (G4S) X4 linker that operably links the VH and VL, regardless of the V-region orientation (LH or HL). The remaining position in the tri-specific protein, Domain 2 (D2), consists of an IgG1 heavy chain, VH-CH1-Hinge-CH2-CH3, and its corresponding light chain, VL-CL, which can be either a kappa or lambda chain. D1 and D2 are genetically linked through a 10 amino acid (G4S)×2 linker, as are D2 and D3 resulting in a contiguous ~125 kDa heavy chain peptide.

When co-transfected with the appropriate light chain, the example symmetric tri-specific peptide can be subsequently purified through the IgG1 Fc (Protein A/Protein G) and assayed to assess functional activity. Heavy and light chain gene "cassettes" were previously constructed such that V-regions could be cloned using either restriction enzyme sites (HindIII/NheI for the heavy chain and HindIII/BsiWI for the light chain) or "restriction-free cloning" such as Gibson Assembly (SGI-DNA, La Jolla, CA), Infusion (Takara Bio USA),) or NEBuilder (NEB, Ipswich, MA), the latter of which was used here.

The application provides methods for making the tri-specific antibody monomers, antigen-binding fragments thereof, and the multi-specific antibodies. In one embodiment, the antibody is a tri-specific antibody. The tri-specific antibody proteins are produced through a process that involves design of the intact molecule, synthesis and cloning of the nucleotide sequences for each domain, expression in mammalian cells and purification of the final product.

Nucleotide sequences were assembled using the Geneious 10.2.3 software package (Biomatters, Auckland, NZ) and broken up into their component domains for gene synthesis (Genewiz, South Plainsfield, NJ). In this example, SI-27X63 (SEQID 52) was split into its component domains where the anti-human ROR1 Ig domain-specific clone 338H4 VLVH scFv occupies D1, anti-human PD-L1 clone PL230C6 occupies D2 (Fab position) and anti-human CD3 clone 284A10 VHVL scFv occupies the C-terminal D3.

Using NEBuilder web-based tools, 5' and 3' nucleotides were appended to each of the domains depending on their position in the larger protein so that each domain overlaps its flanking domains by 20-30 nucleotides which direct site-specific recombination, thus genetically fusing each domain in a single gene assembly step.

A small aliquot was transformed into *E. coli* DH10b (Invitrogen, Carlsbad, CA) and plated on TB+carbenicillin 100 ug/ml plates (Teknova, Hollister, CA) and incubated at 37 C overnight. Resultant colonies were selected and 2 ml overnight cultures inoculated in TB+carbenicillin. DNA was prepared (Thermo-Fisher, Carlsbad, CA) from overnight cultures and subsequently sequenced (Genewiz, South Plainsfield, NJ) using sequencing primers (Sigma, St. Louis, MO) flanking each domain. All DNA sequences were assembled and analysed in Geneious.

In another aspect, the application provides pharmaceutical compositions including the tri-specific antibody monomers, the multi-specific antibodies, the antigen-binding fragments, and the immuno-conjugates thereof. Formulation of the pharmaceutical composition can be accomplished according to standard methodology know to those of ordinary skill in the art.

In one embodiment, the antibodies and monomers according to the disclosure can be prepared in a physiologically acceptable formulation and may comprise a pharmaceutically acceptable carrier, diluent and/or excipient using known techniques. For example, the antibody as described herein may include any functionally equivalent antibody or functional parts thereof, in particular, the monoclonal antibody including any functionally equivalent antibody or functional parts thereof is combined with a pharmaceutically acceptable carrier, diluent and/or excipient to form a therapeutic composition.

With respect to the formulation of suitable compositions for administration to a subject such as a human patient in need of treatment, the antibodies disclosed herein may be mixed or combined with pharmaceutically acceptable carriers known in the art dependent upon the chosen route of administration. There are no particular limitations to the modes of application of the antibodies disclosed herein, and the choice of suitable administration routes and suitable compositions are known in the art without undue experimentation.

Suitable pharmaceutical carriers, diluents and/or excipients are well known in the art and include, for example, phosphate buffered saline solutions, water, emulsions such as oil/water emulsions.

"Pharmaceutically acceptable" refers to those compounds, materials, compositions, and dosage forms which are, within the scope of sound medical judgment, suitable for use contact with the tissues of human beings or animals without excessive toxicity, irritation, or other problem or complication, commensurate with a reasonable benefit/risk ratio.

In one embodiment, the pharmaceutical composition may include proteinaceous carriers such as, for example, serum albumin or immunoglobulin, particularly of human origin. Further biologically active agents may be present in the pharmaceutical composition of the disclosure dependent on the intended use. In one embodiment, the proteinaceous pharmaceutically active matter may be present in amounts between 1 ng and 10 mg per dose. Generally, the regime of administration should be in the range of between 0.1 μg and 10 mg of the antibody according to the disclosure, particularly in a range 1.0 μg to 1.0 mg, and more particularly in a range of between 1.0 μg and 100 μg, with all individual numbers falling within these ranges also being part of the disclosure. If the administration occurs through continuous infusion a more proper dosage may be in the range of between 0.01 μg and 10 mg units per kilogram of body weight per hour with all individual numbers falling within these ranges also being part of the disclosure.

The compositions may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumour site, or may be implanted for systematic release of the therapeutic composition, for example, subcutaneously.

Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

It is well known to those of ordinary skill in the art that the dosage of the composition will depend on various factors such as, for example, the condition of being treated, the particular composition used, and other clinical factors such as weight, size, sex and general health condition of the patient, body surface area, the particular compound or composition to be administered, other drugs being administered concurrently, and the route of administration.

The term “therapeutically effective amount” or “effective amount” refers to the amount of antibody which, when administered to a human or animal, elicits a response which is sufficient to result in a therapeutic effect in said human or animal, e.g., to ameliorate disease in a subject. The effective amount is readily determined by one of ordinary skill in the art following routine procedures. Where the disease is a cancer, the effective amount of the drug may inhibit (for example, slow to some extent, inhibit or stop) one or more of the following example characteristics including, without limitation, cancer cell growth, cancer cell proliferation, cancer cell motility, cancer cell infiltration into peripheral organs, tumor metastasis, and tumor growth. Wherein the disease is a caner, the effective amount of the drug may alternatively do one or more of the following when administered to a subject: slow or stop tumor growth, reduce tumor size (for example, volume or mass), relieve to some extent one or more of the symptoms associated with the cancer, extend progression free survival, result in an objective response (including, for example, a partial response or a complete response), and increase overall survival time. To the extent the drug may prevent growth and/or kill existing cancer cells, it is cytostatic and/or cytotoxic.

A person skilled in the art have the ability to determine the effective amount or concentration of the antibodies disclosed therein to effective treat a condition such as a cancer. Other parameters such as the proportions of the various components in the pharmaceutical composition, administration does and frequency may be obtained by a person skilled in the art without undue experimentation. For example, a suitable solution for injection may contain, without limitation, from about 1 to about 20, from about 1 to about 10 mg antibodies per ml. The example dose may be, without limitation, from about 0.1 to about 20, from about 1 to about 5 mg/Kg body weight. The example administration frequency could be, without limitation, once per day or three times per week.

The compositions may be administered by standard routes of administration. In general, the composition may be administered by topical, oral, rectal, nasal, intradermal, intraperitoneal, or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumour. The method includes administration of a single dose, administration of repeated doses at predetermined time intervals, and sustained administration for a predetermined period of time.

Although many forms of administration are possible, an example administration form would be a solution for injection, in particular for intravenous or intra-arterial injection. Usually, a suitable pharmaceutical composition for injection may include pharmaceutically suitable carriers or excipients such as, without limitation, a buffer, a surfactant, or a stabilizer agent. Example buffers may include, without limitation, acetate, phosphate or citrate buffer. Example surfactants may include, without limitation, polysorbate. Example stabilizer may include, without limitation, human albumin.

In one embodiment, the administration may be parenterally, e.g. intravenously. Preparations for parenteral administration include sterile aqueous or non-aqueous solutions, suspensions and emulsions. Non-aqueous solvents include without being limited to it, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer’s dextrose, dextrose and sodium chloride, lactated Ringer’s, or fixed oils. Intravenous vehicles include fluid and nutrient replenishers, electrolyte replenishers (such as those based on Ringer’s dextrose) and others. Preservatives may also be present such as, for example, antimicrobials, anti-oxidants, chelating agents, inert gases, etc.

The antibody monomers, antibodies, antigen-binding fragments and immuno-conjugates thereof may be used in combination with a therapeutic agent or a composition comprising a therapeutic agent for treatment purpose. In some embodiments, the multi-specific antibody molecule is used in combination with one or more additional therapeutic agents at an effective amount. The additional therapeutic agent includes an antibody, a chemotherapy agent, an enzyme, or a combination thereof. In some embodiment, the additional therapeutic agent can be an anti-estrogen agent, a receptor tyrosine kinase inhibitor, a kinase inhibitor, a cell cycle inhibitor, a DNA, RNA or protein synthesis inhibitor, a RAS inhibitor, or a combination thereof. In some embodiments, the additional therapeutic agent can be a check point inhibitor. In some embodiments, therapeutic agent comprises inhibitors of PD1, PDL1, CTLA4, 4-1BB, OX40, GITR, ICOS, LIGHT, TIM3, LAG3, TIGIT, CD40, CD27, HVEM, BTLA, VISTA, B7H4, CSF1R, NKG2D, CD73, a derivative or a combination thereof.

In one embodiment, the therapeutic agent may capecitabine, cisplatin, Cyclophosphamide, methotrexate, 5-fluorouracil, Doxorubicin, cyclophosphamide, Mustine, vincristine, procarbazine, prednisolone, bleomycin, vinblastine, dacarbazine, etoposide, Epirubicin, pemetrexed, folinic acid, gemicitabine, oxaliplatin, irinotecan, topotecan, camptothecin, docetaxel, paclitaxel, fulvestrant, tamoxifen, letrozole, exemestane, anastrozole, aminoglutethimide, testolactone, vorozole, formestane, fadrozole, erlotinib, lafatinib, dasatinib, gefitinib, osimertinib, vandertanib, afatinib, imatinib, pazopinib, lapatinib, sunitinib, nilotinib, sorafenib, nab-palitaxel, Everolimus, temsirolimus, Dabrafenib, vemurafenib, trametinib, vintafolide, apatinib, crizotinib, periforsine, olaparib, Bortezomib, tofacitinib, trastuzumab, a derivative or a combination thereof.

Cancers, including breast cancer, colorectal cancer, pancreatic cancer, head and neck cancer, melanoma, ovarian cancer, prostate cancer, non-small lung cell cancer, glioma, esophageal cancer, nasopharyngeal cancer, anal cancer, rectal cancer, gastric cancer, bladder cancer, cervical cancer, or brain cancer, may express cancer-associated genes. Inhibition of cancer-associated activity with specific monoclonal antibodies or antigen-binding fragment may have therapeutic effect on cancers. Furthermore, administering a therapeutically effective amount of composition comprising monoclonal antibodies or antigen-binding fragment specific for cancer-associated protein may cure, prevent, ameliorate, and delay the development or metastasis of cancers, through the effect of the cytotoxic agent.

The present disclosure may be understood more readily by reference to the following detailed description of specific embodiments and examples included herein. Although the present disclosure has been described with reference to specific details of certain embodiments thereof, it is not intended that such details should be regarded as limitations upon the scope of the disclosure.

EXAMPLES

Example 1: FACS Analysis of Tri-Specific Antibody Binding to ROR1 Expressing CHO Cells The tri-specific antibodies listed in tables 1 and 2 were tested for binding to Chinese hamster ovary cells (CHO) cells stably expressing full length human ROR1. Antibodies were prepared at 2× final concentration and titrated 1:3 across 8 wells of a 96 well plate in 50 ul of PBS/2% FBS and then 5,000 ROR1-CHO cells in 50 ul PBS/2% FBS were added. This mixture was incubated for 30 minutes on ice, washed once with 200 ul PBS/2% FBS, and then the secondary antibody PE Goat anti-Human IgG Fc at 1:1000 dilution of stock was added, and this mixture was incubated for 30 minutes on ice. Cells were washed 2×200 ul PBS/2% FBS, resuspended in 50 ul PBS/2% FBS and analyzed on a BD LSRFORTESSA and the binding profile is shown in FIG. 4. All of the tri-specific antibodies that contained a ROR1 binding domain bound at varying levels to the CHO-ROR1 cells.

Example 2: FACS Analysis of Tri-Specific Antibody Binding to PD-L1 Expressing CHO Cells The tri-specific antibodies listed in tables 1 and 2 were tested for binding to Chinese hamster ovary cells (CHO) cells stably expressing full length human PD-L1. Antibodies were prepared at 2× final concentration and titrated 1:3 across 8 wells of a 96 well plate in 50 ul of PBS/2% FBS and then 5,000 PD-L1-CHO cells in 50 ul PBS/2% FBS were added. This mixture was incubated for 30 minutes on ice, washed once with 200 ul PBS/2% FBS, and then the secondary antibody PE Goat anti-Human IgG Fc at 1:1000 dilution of stock was added, and this mixture was incubated for 30 minutes on ice. Cells were washed 2×200 ul PBS/2% FBS, resuspended in 50 ul PBS/2% FBS and analyzed on a BD LSRFORTESSA and the binding profile is shown in FIG. 5. All of the tri-specific antibodies that contained a PD-L1 binding domain bound at similar levels to the CHO-PD-L1 cells.

Example 3: Re-Directed T Cell Cytotoxicity (RTCC) Assay with CD3+ T Cells as Effectors and B-Acute Lymphoblastic Leukemia (B-ALL) Cell Line Kasumi-2 as Targets The tri-specific antibodies listed in tables 1 and 2 were tested for RTCC activity against the B-ALL cell line Kasumi 2 using human CD3+ T cells as effectors. The Kasumi 2 target cells, 5×10e6, were labeled with CFSE (Invitrogen, #C34554) at 0.5 uM in 10 ml of culture media for 20 minutes at 37 C. The cells were washed 3 times with 50 ml of culture media before resuspending in 10 ml then counted again. Antibodies were prepared at 4× final concentration and titrated 1:10 across 10 wells of a 96 well plate in 200 ul of RPMI+10% FBS. Human CD3+ T cells were enriched from peripheral blood mononuclear cells from a normal donor using the EasySep™ Human T Cell Enrichment Kit (Stemcell Technologies, #19051) as per the manufacturers protocol. The final cell population was determined to be 98% CD3+ T cells by FACS analysis (data not shown). In the final destination 96 well plate the target cells, T cells, and serially titrated antibodies were combined by adding 100 ul of target cells (5,000), 50 ul of CD3+ T cells (50,000), and 50 ul of each antibody dilution to each well of the assay. The assay plate was incubated at 37 C for approximately 72 hours and then the contents of each assay well were harvested and analyzed for the number of CFSE-labeled target cells remaining. As shown on FIG. 6, all of the tri-specific antibodies that contained a ROR1 binding domain potently killed the target cells at less than 0.01 nM or 10 pM except for the control SI-27X62 which has a FITC binding domain in the C-terminal domain 3 position which does not bind to CD3+ T cells.

Example 4: Re-Directed T Cell Cytotoxicity (RTCC) Assay with CD4+ T Regulatory Cells as Effectors and B-Acute Lymphoblastic Leukemia (B-ALL) Cell Line Kasumi-2 as Targets The tri-specific antibodies listed in tables 1 and 2 were tested for RTCC activity against the B-ALL cell line Kasumi 2 using human CD4+ T regulatory cells as effectors. The Kasumi 2 target cells, 5×10e6, were labeled with CFSE (Invitrogen, #C34554) at 0.5 uM in 10 ml of culture media for 20 minutes at 37 C. The cells were washed 3 times with 50 ml of culture media before resuspending in 10 ml then counted again. Antibodies were prepared at 4× final concentration and titrated 1:10 across 10 wells of a 96 well plate in 200 ul of RPMI+10% FBS. Human CD4+ T regulatory cells were generated using the EasySep™ Human CD4+ CD127lowCD25+ Regulatory T Cell Isolation Kit (Stemcell #18063) as per the manufacturers protocol. Enriched T regulatory cells were stimulated using Miltenyi CD3/CD28 activation beads (#-130-095-353) and cultured for 14 days in complete RPMI, supplemented with 5% human serum and 500 U/ml recombinant human IL-2 (Peprotech #200-02). The final population of T regulatory cells were analyzed by FACS to be more than 90% CD127low $CD25^{++}$ (Data not shown). In the final destination 96 well plate the target cells, T cells, and serially titrated antibodies were combined by adding 100 ul of target cells (5,000), 50 ul of CD4+ T regulatory cells (50,000), and 50 ul of each antibody dilution to each well of the assay. The assay plate was incubated at 37 C for approximately 72 hours and then the contents of each assay well were harvested and analyzed for the number of CFSE-labeled target cells remaining. As shown on FIG. 7, all of the tri-specific antibodies that contained a ROR1 binding domain potently killed the target cells at less than 0.1 nM or 100 pM except for the control SI-27X62 which has a FITC binding domain in the C-terminal domain 3 position which does not bind to CD3+ T cells.

Example 5: Re-Directed T Cell Cytotoxicity (RTCC) Assay with "Exhausted" CD8+ T Cells as Effectors and B-Acute Lymphoblastic Leukemia (B-ALL) Cell Line Kasumi-2 as Targets The tri-specific antibodies listed in tables 1 and 2 were tested for RTCC activity against the B-ALL cell line Kasumi 2 using "exhausted" human CD8+ T cells as effectors. The Kasumi 2 target cells, 5×10e6, were labeled with CFSE (Invitrogen, #C34554) at 0.5 uM in 10 ml of culture media for 20 minutes at 37 C. The cells were washed 3 times with 50 ml of culture media before resuspending in 10 ml then counted again. Antibodies were prepared at 4× final concentration and titrated 1:10 across 10 wells of a 96 well plate in 200 ul of RPMI+10% FBS. Human CD8+ T cells were enriched using the EasySep™ Human CD8+ T Cell Enrichment Kit (Stemcell #19053) as per the manufacturers protocol. Enriched CD8+ T cells were stimulated using Miltenyi CD3/CD28 activation beads (#-130-095-353) and cultured for 7 days in complete RPMI, supplemented with 5% human serum and 500 U/ml recombinant human IL-2 (Peprotech #200-02). The final population of exhausted CD8+ T cells were analyzed by FACS to be more than 95% CD8+ cells expressing several markers of exhaustion e.g., PD-1, TIGIT, TIM-3, and LAG-3 (Data not shown). In the final destination 96 well plate the target cells, T cells, and serially titrated antibodies were combined by adding 100 ul of target cells (5,000), 50 ul of exhausted CD8+ T cells (50,000), and 50 ul of each antibody dilution to each well of the assay. The assay plate was incubated at 37 C for approximately 72 hours and then the contents of each assay well were harvested and analyzed for the number of CFSE-labeled target cells remaining. As shown on FIG. 8, the tri-specific antibodies that contained the 338H4 ROR1 binding domain potently killed the target cells at less than 0.01 nM or 10 pM whereas those antibodies with the R11 or 323H7 ROR1 binding domain only weakly killed the target cells and the control SI-27X62 which has a FITC binding domain in the C-terminal domain 3 position which does not bind to CD3+ T cells showed negative killing activity.

Example 6: Re-Directed T Cell Cytotoxicity (RTCC) Assay with Peripheral Blood Mononuclear Cells as Effectors and the U87 Human Glioblastoma Cell Line Transfected with the Epidermal Growth Factor viii (EGFRviii) Mutant as Targets The tri-specific antibodies listed in tables 1 and 2 were tested for RTCC activity against the U87-EGFRviii cell line using human PBMC as effectors. The U87-EGFR viii was transduced with the NucLight Red Lentivirus (IncuCyte®) to generate a cell line that stably expresses the fluorescent mKate2 protein (Shcherbo et al., 2009, J. Biochem, 418(3): 567-574). Antibodies were prepared at 4× final concentration and titrated 1:10 across 3 wells of a 96 well plate in 200 ul of RPMI+10% FBS. Human PBMC were purified by standard ficoll density gradient from a "leukopak" which is an enriched leukapheresis product collected from normal human peripheral blood. In the final destination 96 well plate the target cells, PBMC, and serially titrated antibodies were combined by adding 100 ul of target cells (5,000), 50 ul of PBMC (200,000), and 50 ul of each antibody dilution to each well of the assay. The assay plate was incubated at 37 C for approximately 72 hours and then the contents of each assay well were harvested and analyzed for the number of NucLight Red target cells remaining. As shown in FIG. 9, the set of tri-specific molecules with the configuration of PL230×806×480C8 directed potent killing of target cells at 10 pM or more antibody. The control antibody, SI-37X3 FITC×806×480C8 which does not contain the PD-L1 binding domain PL230C6 also potently killed target cells but with slightly lower potency that the tri-specific antibody with the PD-L1 binding domain, SI-37X1 PL230C6×806×480C8. The control tri-specific antibody SI-27X109 PL230C6×FITC×480C8 which does not contain the EGFRviii binding domain 806 showed much weaker killing of target cells and the control tri-specific antibody SI-37X4 PL230C6×806×FITC that does not contain the CD3 binding domain 480C8 showed negligible killing of target cells. As shown in FIG. 10, the set of tri-specific molecules with the configuration of 806×PL230C6×480C8 directed potent killing of target cells at 10 pM or more antibody with the tri-specific antibody SI-37X2 806×PL230C6×480C8 being more potent than the 3 control tri-specific antibodies with a FITC binding domain in each of the 3 positions of the tri-specific.

Example 7: Re-Directed T Cell Cytotoxicity Assay with PBMC Cells as Effectors and CD19 Positive B-Acute Lymphoblastic Leukemia Cell Line Kasumi-2 as Targets The tri-specific antibodies listed in tables 1 and 2 were tested for RTCC activity against the B-ALL cell line Kasumi 2 using PBMC as effectors. The Kasumi 2 target cells, 5×10e6, were labeled with CFSE (Invitrogen, #C34554) at 0.5 uM in 10 ml of culture media for 20 minutes at 37 C. The cells were washed 3 times with 50 ml of culture media before resuspending in 10 ml then counted again. Antibodies were prepared at 4× final concentration and titrated 1:10 across 10 wells of a 96 well plate in 200 ul of RPMI+10% FBS. Human PBMC were purified by standard ficoll density gradient from a "leukopak" which is an enriched leukapheresis product collected from normal human peripheral blood. In the final destination 96 well plate the target cells, T cells, and serially titrated antibodies were combined by adding 100 ul of target cells (5,000), 50 ul of PBMC (50,000), and 50 ul of each antibody dilution to each well of the assay. The assay plate was incubated at 37 C for approximately 72 hours and then the contents of each assay well were harvested and analyzed for the number of CFSE-labeled target cells remaining. As shown on FIG. 10, the tri-specific antibody SI34X2 21D4×PL230C6×480C8 potently killed the target cells at less than 0.01 nM compared to the 3 control tri-specific antibodies with a FITC binding domain in each of the 3 positions of the tri-specific.

While the present disclosure has been described with reference to particular embodiments or examples, it may be understood that the embodiments are illustrative and that the disclosure scope is not so limited. Alternative embodiments of the present disclosure may become apparent to those having ordinary skill in the art to which the present disclosure pertains. Such alternate embodiments are considered to be encompassed within the scope of the present disclosure. Accordingly, the scope of the present disclosure is defined by the appended claims and is supported by the foregoing description. All references cited or referred to in this disclosure are hereby incorporated by reference in their entireties.

MULTI-SPECIFIC ANTIBODIES AND METHODS OF MAKING AND USING THEREOF
SEQUENCE LISTING
The antibody complementary Determining Regions (CDR) are defined using the KABAT numbering system and are underlined in the amino acid (aa) sequence listing:
Light Chain
CDR1: residues 24-34
CDR2: residues 50-56
CDR3: residues 89-97
Heavy Chain
CDR1: residues 31-35
CDR2: residues 50-65
CDR3: residues 95-102 anti-ROR1 R11 VH nt

> SEQ ID NO: 1

CAGTCCGTGAAGGAGTCCGAGGGCGACCTGGTGACCCCCGCCGGCAACCTGACCCTGACCTGCACCGCCTCCGGC

TCCGACATCAACGACTACCCCATCTCCTGGGTGCGGCAGGCCCCCGGCAAGGGCCTGGAGTGGATCGGCTTCATC

AACTCCGGCGGCTCCACCTGGTACGCCTCCTGGGTGAAGGGCCGGTTCACCATCTCCCGGACCTCCACCACCGTGG

ACCTGAAGATGACCTCCCTGACCACCGACGACACCGCCACCTACTTCTGCGCCCGGGGCTACTCCACCTACTACGG

CGACTTCAACATCTGGGGCCCCGGCACCCTGGTGACCATCTCCTCG anti-ROR1 R11 VH aa

> SEQ ID NO: 2

QSVKESEGDLVTPAGNLTLTCTASGSDINDYPISWVRQAPGKGLEWIGFINSGGSTWYASWVKGRFTISRTSTTVD

LKMTSLTTDDTATYFCARGYSTYYGDFNIWGPGTLVTISS anti-ROR1 R11 VL nt

> SEQ ID NO: 3

GAGCTGGTGATGACCCAGACCCCCTCCTCCACCTCCGGCGCCGTGGGCGGCACCGTGACCATCAACTGCCAGGCC

TCCCAGTCCATCGACTCCAACCTGGCCTGGTTCCAGCAGAAGCCCGGCCAGCCCCCCACCCTGCTGATCTACCGGG

CCTCCAACCTGGCCTCCGGCGTGCCCTCCCGGTTCTCCGGCTCCCGGTCCGGCACCGAGTACACCCTGACCATCTCC

GGCGTGCAGCGGGAGGACGCCGCCACCTACTACTGCCTGGGCGGCGTGGGCAACGTGTCCTACCGGACCTCCTTC

GGCGGCGGCACCGAGGTGGTGGTGAAG anti-ROR1 R11 VL aa

> SEQ ID NO: 4

ELVMTQTPSSTSGAVGGTVTINCQASQSIDSNLAWFQQKPGQPPTLLIYRASNLASGVPSRFSGSRSGTEYTLTISG

VQREDAATYYCLGGVGNVSYRTSFGGGTEVVVK anti-ROR1 323H7 VHv4 nt

> SEQ ID NO: 5

GAGGTGCAGCTGTTGGAGTCTGGGGGAGGCTTGGTACAGCCTGGGGGGTCCCTGAGACTCTCCTGTGCAGCCTCT

GGATTCACCATCAGTCGCTACCACATGACTTGGGTCCGCCAGGCTCCAGGGAAGGGGCTGGAGTGGATCGGACAT

ATTTATGTTAATAATGATGACACAGACTACGCGAGCTCCGCGAAAGGCCGGTTCACCATCTCCAGAGACAATTCCA

AGAACACGCTGTATCTGCAAATGAACAGCCTGAGAGCCGAGGACACGGCCACCTATTTCTGTGCGAGATTGGATG

TTGGTGGTGGTGGTGCTTATATTGGGGACATCTGGGGCCAGGGAACTCTGGTTACCGTCTCTTCA

> SEQ ID NO: 6 anti-ROR1 323H7 VHv4 aa
EVQLLESGGGLVQPGGSLRLSCAASGFTISRYHMTWVRQAPGKGLEWIGHIYVNNDDTDYASSAKGRFTISRDNS

KNTLYLQMNSLRAEDTATYFCARLDVGGGGAYIGDIWGQGTLVTVSS anti-ROR1 323H7 VLv1 nt

> SEQ ID NO: 7

GACATCCAGATGACCCAGTCTCCATCCTCCCTGTCTGCATCTGTAGGAGACAGAGTCACCATCACTTGCCAGTCCA

GTCAGAGTGITTATAACAACAACGACTTAGCCTGGTATCAGCAGAAACCAGGGAAAGTTCCTAAGCTCCTGATCTA

TTATGCTTCCACTCTGGCATCTGGGGTCCCATCTCGGTTCAGTGGCAGTGGATCTGGGACAGATTTCACTCTCACCA

TCAGCAGCCTGCAGCCTGAAGATGTTGCAACTTATTACTGTGCAGGCGGTTATGATACGGATGGTCTTGATACGTT

TGCTTTCGGCGGAGGGACCAAGGTGGAGATCAAA

-continued anti-ROR1 323H7 VLv1 aa

> SEQ ID NO: 8

DIQMTQSPSSLSASVGDRVTITCQSSQSVYNNNDLAWYQQKPGKVPKLLIYYASTLASGVPSRFSGSGSGTDFTLTI

SSLQPEDVATYYCAGGYDTDGLDTFAFGGGTKVEIK anti-ROR1 338H4 VHv3 nt

> SEQ ID NO: 9

GAGGTGCAGCTGGTGGAGTCTGGGGGAGGCTTGGTCCAGCCTGGGGGGTCCCTGAGACTCTCCTGTACTGCCTCT

GGATTCTCCCTCAGTAGCTATGCAATGAGCTGGGTCCGCCAGGCTCCAGGGAGGGGGCTGGAGTGGATCGGAAT

CATTTATGCTAGTGGTAGCACATACTACGCGAGCTCGGCGAAAGGCAGATTCACCATCTCCAAAGACAATACCAAG

AACACGGTGGATCTTCAAATGAACAGCCTGAGAGCCGAGGACACGGCTGTGTATTACTGTGCGAGAATTTATGAC

GGCATGGACCTCTGGGGCCAGGGAACTCTGGTTACCGTCTCTTCA anti-ROR1 338H4 VHv3 aa

> SEQ ID NO: 10

EVQLVESGGGLVQPGGSLRLSCTASGFSLSSYAMSWVRQAPGRGLEWIGIIYASGSTYYASSAKGRFTISKDNTKNTVDL

QMNSLRAEDTAVYYCARIYDGMDLWGQGTLVTVSS

> SEQ ID NO: 11 anti-ROR1 338H4 VLv4 nt

GACATCCAGATGACCCAGTCTCCATCCTCCCTGTCTGCATCTGTAGGAGACAGAGTCACCATCAATTGCCAGGCCA

GTCAGAACATTTACAGCTACTTATCCTGGTATCAGCAGAAACCAGGGAAAGTTCCTAAGCGCCTGATCTATCTGGC

ATCTACTCTGGCATCTGGGGTCCCATCTCGGTTCAGTGGCAGTGGATCTGGGACAGATTACACTCTCACCATCAGC

AGCCTGCAGCCTGAAGATGTTGCAACTTATTACTGTCAAAGCAATTATAACGGTAATTATGGTTTCGGCGGAGGGA

CCAAGGTGGAGATCAAA anti-ROR1 338H4 VLv4 aa

> SEQ ID NO: 12

DIQMTQSPSSLSASVGDRVTINCQASQNIYSYLSWYQQKPGKVPKRLIYLASTLASGVPSRFSGSGSGTDYTLTISS

LQPEDVATYYCQSNYNGNYGFGGGTKVEIK anti-PD-L1 PL230C6 VHv3 nt

>SEQ ID: 13

CAGTCGGTGGAGGAGTCTGGGGGAGGCTTGGTCCAGCCTGGGGGGTCCCTGAGACTCTCCTGTACAGCCTCTGG

AATCGACCTTAATACCTACGACATGATCTGGGTCCGCCAGGCTCCAGGCAAGGGGCTAGAGTGGGTTGGAATCAT

TACTTATAGTGGTAGTAGATACTACGCGAACTGGGCGAAAGGCCGATTCACCATCTCCAAAGACAATACCAAGAA

CACGGTGTATCTGCAAATGAACAGCCTGAGAGCTGAGGACACGGCTGTGTATTACTGTGCCAGAGATTATATGAG

TGGTTCCCACTTGTGGGGCCAGGGAACCCTGGTCACCGTCTCTAGT anti-PD-L1 PL230C6 VHv3 aa

>SEQ ID: 14

QSVEESGGGLVQPGGSLRLSCTASGIDLNTYDMIWVRQAPGKGLEWVGIITYSGSRYYANWAKGRFTISKDNTKN

TVYLQMNSLRAEDTAVYYCARDYMSGSHLWGQGTLVTVSS anti-PD-L1 PL230C6 VLv2 nt

>SEQ ID: 15

GCCTATGATATGACCCAGTCTCCATCTTCCGTGTCTGCATCTGTAGGAGACAGAGTCACCATCAAGTGTCAGGCCA

GTGAGGACATTTATAGCTTCTTGGCCTGGTATCAGCAGAAACCAGGGAAAGCCCCTAAGCTCCTGATCCATTCTGC

ATCCTCTCTGGCATCTGGGGTCCCATCAAGGTTCAGCGGCAGTGGATCTGGGACAGATTTCACTCTCACCATCAGC

AGCCTGCAGCCTGAAGATTTTGCAACTTACTATTGTCAACAGGGTTATGGTAAAAATAATGTTGATAATGCTTTCG

GCGGAGGGACCAAGGTGGAGATCAAA anti-PD-L1 PL230C6 VLv2 aa

>SEQ ID: 16

AYDMTQSPSSVSASVGDRVTIKCQASEDIYSFLAWYQQKPGKAPKLLIHSASSLASGVPSRFSGSGSGTDFTLTIS

SLQPEDFATYYCQQGYGKNNVDNAFGGGTKVEIK

-continued anti-CD3 12C VH nt >SEQ ID: 17

CAGGTGCAATTGGTGGAAAGCGGAGGGGGACTGGTGCAGCCCGGGGGAAGTCTGAAGCTGTCCTGTGCCGCCA
GCGGCTTTACCTTCAACAAGTACGCCATGAATTGGGTCCGACAGGCCCCAGGGAAAGGCCTGGAATGGGTGGCA
CGGATTCGGTCCAAGTACAACAACTACGCCACCTACTACGCTGACTCCGTGAAGGACAGATTCACCATCAGCCGGG
ACGACTCTAAGAACACCGCCTATCTGCAGATGAACAACCTGAAAACCGAGGATACAGCTGTGTACTATTGTGTGCG
GCACGGCAACTTCGGCAACTCCTACATCTCCTACTGGGCCTATTGGGGACAGGGAACACTGGTCACCGTGTCTAGC anti-CD3 12C VH aa >SEQ ID: 18

QVQLVESGGGLVQPGGSLKLSCAASGFTFNKYAMNWVRQAPGKGLEWVARIRSKYNNYATYYADSVKDRFTISRDDS
KNTAYLQMNNLKTEDTAVYYCVRHGNFGNSYISYWAYWGQGTLVTVSS anti-CD3 12C VL nt >SEQ ID: 19

CAGACCGTGGTCACCCAGGAACCTTCCCTGACCGTCTCCCCAGGCGGCACCGTGACCCTGACCTGTGGCTCCTCTA
CCGGCGCTGTGACCTCCGGCAACTACCCTAACTGGGTGCAGCAGAAACCCGGACAGGCTCCTAGAGGCCTGATCG
GCGGCACCAAGTTTCTGGCCCCTGGCACCCCTGCCAGATTCTCCGGCTCCCTGCTGGGAGGCAAGGCCGCTCTGAC
CCTGTCTGGCGTGCAGCCTGAGGACGAGGCCGAGTACTACTGTGTGCTGTGGTACTCCAACAGATGGGTGTTCGG
AGGCGGCACAAAGCTGACCGTGCTGTCCTCG anti-CD3 12C VL aa >SEQ ID: 20

QTVVTQEPSLTVSPGGTVTLTCGSSTGAVTSGNYPNWVQQKPGQAPRGLIGGTKFLAPGTPARFSGSLLGGKAA
LTLSGVQPEDEAEYYCVLWYSNRWVFGGGTKLTVLSS anti-CD3 284A10 VHv1 nt >SEQ ID: 21

GAGGTGCAGCTGGTGGAGTCTGGGGGAGGCTTGGTCCAGCCTGGGGGGTCCCTGAGACTCTCCTGTGCAGCCTC
TGGATTCACCATCAGTACCAATGCAATGAGCTGGGTCCGCCAGGCTCCAGGGAAGGGGCTGGAGTGGATCGGAG
TCATTACTGGTCGTGATATCACATACTACGCGAGCTGGGCGAAAGGCAGATTCACCATCTCCAGAGACAATTCCAA
GAACACGCTGTATCTTCAAATGAACAGCCTGAGAGCCGAGGACACGGCTGTGTATTACTGTGCGCGCGACGGTGG
ATCATCTGCTATTACTAGTAACAACATTTGGGGCCAAGGAACTCTGGTCACCGTTTCTTCA anti-CD3 284A10 VHv1 aa >SEQ ID: 22

EVQLVESGGGLVQPGGSLRLSCAASGFTISTNAMSWVRQAPGKGLEWIGVITGRDITYYASWAKGRFTISRDNSKN
TLYLQMNSLRAEDTAVYYCARDGGSSAITSNNIWGQGTLVTVSS anti-CD3 284A10 VLv1 nt >SEQ ID: 23

GACGTCGTGATGACCCAGTCTCCTTCCACCCTGTCTGCATCTGTAGGAGACAGAGTCACCATCAATTGCCAAGCCA
GTGAGAGCATTAGCAGTTGGTTAGCCTGGTATCAGCAGAAACCAGGGAAAGCCCCTAAGCTCCTGATCTATGAAG
CATCCAAACTGGCATCTGGGGTCCCATCAAGGTTCAGCGGCAGTGGATCTGGGACAGAGTTCACTCTCACCATCA
GCAGCCTGCAGCCTGATGATTTTGCAACTTATTACTGCCAAGGCTATTTTTATTTTATTAGTCGTACTTATGTAA
ATTCTTTCGGCGGAGGGACCAAGGTGGAGATCAAA anti-CD3 284A10 VLv1 aa >SEQ ID: 24

DVVMTQSPSTLSASVGDRVTINCQASESISSWLAWYQQKPGKAPKLLIYEASKLASGVPSRFSGSGSGTEFTLTISS
LQPDDFATYYCQGYFYFISRTYVNSFGGGTKVEIK anti-CD3 299F6 VHv2 nt >SEQ ID: 25

GAGGTGCAGCTGGTGGAGTCTGGGGGAGGCTTGGTCCAGCCTGGGGGGTCCCTGAGACTCTCCTGTACGGCCTC
TGGATTCACCATCAGTAGCAATGCAATGAGCTGGGTCCGCCAGGCTCCAGGGAAGGGGCTGGAGTGGATCGGAG
TCATTACTGGTCGTGATATCACATACTACGCGAGCTGGGCGAAAGGCAGATTCACCATCTCCAAAGACACCTCCAA

-continued

GAACACGGTGGATCTTCAAATGAACAGCCTGAGAGCCGAGGACACGGCTGTGTATTACTGTGCGCGCGACGGTG

GATCATCTGCTATTACTAGTAACAACATTTGGGGCCAAGGAACTCTGGTCACCGTTTCTTCA anti-CD3 299F6 VHv2 aa

>SEQ ID: 26

EVQLVESGGGLVQPGGSLRLSCTASGFTISSNAMSWVRQAPGKGLEWIGVITGRDITYYASWAKGRFTISKDTSKNT

VDLQMNSLRAEDTAVYYCARDGGSSAITSNNIWGQGTLVTVSS anti-CD3 299F6 VLv1 nt

>SEQ ID: 27

GACATCCAGATGACCCAGTCTCCTTCCACCCTGTCTGCATCTGTAGGAGACAGAGTCACCATCACTTGCCAAGCCA

GTGAGAGCATTAGCAGTTGGTTAGCCTGGTATCAGCAGAAACCAGGGAAAGCCCCTAAGCTCCTGATCTATGAAG

CATCCAAACTGGCATCTGGGGTCCCATCAAGGTTCAGCGGCAGTGGATCTGGGACAGAGTTCACTCTCACCATCA

GCAGCCTGCAGCCTGATGATTTTGCAACTTATTACTGCCAAGGCTATTTTTATTTTATTAGTCGTAGTTATGTAA

ATGCTTTCGGCGGAGGGACCAAGGTGGAGATCAAA anti-CD3 299F6 VLv1 aa

>SEQ ID: 28

DIQMTQSPSTLSASVGDRVTITCQASESISSWLAWYQQKPGKAPKLLIYEASKLASGVPSRFSGSGSGTEFTLTISS

LQPDDFATYYCQGYFYFISRSYVNAFGGGTKVEIK anti-CD3 480C8 VHv1 nt

>SEQ ID: 29

GAGGTGCAGCTGGTGGAGTCTGGGGGAGGCTTGGTCCAGCCTGGGGGGTCCCTGAGACTCTCCTGTGCAGCCTC

TGGAATCGACCTCAGTAGCAATGCAATGAGCTGGGTCCGCCAGGCTCCAGGGAAGGGGCTGGAGTGGATCGGAG

TCATTACTGGTCGTGATATCACATACTACGCGAGCTGGGCGAAAGGCAGATTCACCATCTCCAGAGACAATTCCAA

GAACACGCTGTATCTTCAAATGAACAGCCTGAGAGCCGAGGACACGGCTGTGTATTACTGTGCGCGCGACGGTGG

ATCATCTGCTATTAATAGTAAGAACATTTGGGGCCAAGGAACTCTGGTCACCGTTTCTTCA anti-CD3 480C8 VHv1 aa

>SEQ ID: 30

EVQLVESGGGLVQPGGSLRLSCAASGIDLSSNAMSWVRQAPGKGLEWIGVITGRDITYYASWAKGRFTISRDNSKNTLY

LQMNSLRAEDTAVYYCARDGGSSAINSKNIWGQGTLVTVSS anti-CD3 480C8 VHv2 nt

>SEQ ID: 31

GAGGTGCAGCTGGTGGAGTCTGGGGGAGGCTTGGTCCAGCCTGGAGGGTCCCTGAGACTCTCCTGTACGGCCTC

TGGAATCGACCTCAGTAGCAATGCAATGAGCTGGGTCCGCCAGGCTCCAGGGAAAGGGCTGGAGTGGATCGGAG

TCATTACTGGTCGTGATATCACATACTACGCGAGCTGGGCGAAAGGCAGATTCACCATCTCCAAAGACACCTCCAA

GAACACGGTGGATCTTCAAATGAACAGCCTGAGAGCCGAGGACACGGCTGTGTATTACTGTGCGCGCGACGGTG

GATCATCTGCTATTAATAGTAAGAACATTTGGGGCCAAGGAACTCTGGTCACCGTTTCTTCA anti-CD3 480C8 VHv2 aa

>SEQ ID: 32

EVQLVESGGGLVQPGGSLRLSCTASGIDLSSNAMSWVRQAPGKGLEWIGVITGRDITYYASWAKGRFTISKDTSKNTV

DLQMNSLRAEDTAVYYCARDGGSSAINSKNIWGQGTLVTVSS anti-CD3 480C8 VLv1 nt

>SEQ ID: 33

GACATCCAGATGACCCAGTCTCCTTCCACCCTGTCTGCATCTGTAGGAGACAGAGTCACCATCACTTGCCAAGCCA

GTGAGAGCATTAGCAGTTGGTTAGCCTGGTATCAGCAGAAACCAGGGAAAGCCCCTAAGCTCCTGATCTATGAAG

CATCCAAACTGGCATCTGGGGTCCCATCAAGGTTCAGCGGCAGTGGATCTGGGACAGAGTTCACTCTCACCATCA

GCAGCCTGCAGCCTGATGATTTTGCAACTTATTACTGCCAAGGCTATTTTTATTTTATTAGTCGTACTTATGTAAATG

CTTTCGGCGGAGGGACCAAGGTGGAGATCAAA anti-CD3 480C8 VLv1 aa

>SEQ ID: 34

DIQMTQSPSTLSASVGDRVTITCQASESISSWLAWYQQKPGKAPKLLIYEASKLASGVPSRFSGSGSGTEFTLTISSLQPD

DFATYYCQGYFYFISRTYVNAFGGGTKVEIK

-continued anti-FITC 4-4-2-(4420) VH nt

>SEQ ID: 35

GAGGTGAAGCTGGATGAGACTGGAGGAGGCTTGGTGCAACCTGGGAGGCCCATGAAACTCTCCTGTGTTGCCTCT

GGATTCACTTTTAGTGACTACTGGATGAACTGGGTCCGCCAGTCTCCAGAGAAAGGACTGGAGTGGGTAGCACAA

ATTAGAAACAAACCTTATAATTATGAAACATATTATTCAGATTCTGTGAAAGGCAGATTCACCATCTCAAGAGATG

ATTCCAAAAGTAGTGTCTACCTGCAAATGAACAACTTAAGAGTTGAAGACATGGGTATCTATTACTGTACGGGTTC

TTACTATGGTATGGACTACTGGGGTCAAGGAACCTCAGTCACCGTCTCCTCA anti-FITC 4-4-2-(4420) VH aa

>SEQ ID: 36

EVKLDETGGGLVQPGRPMKLSCVASGFTFSDYWMNWVRQSPEKGLEWVAQIRNKPYNYETYYSDSVKGRFTISRDDS

KSSVYLQMNNLRVEDMGIYYCTGSYYGMDYWGQGTSVTVSS anti-FITC 4-4-2-(4420) VL nt

>SEQ ID: 37

GATGTCGTGATGACCCAAACTCCACTCTCCCTGCCTGTCAGTCTTGGAGATCAAGCCTCCATCTCTTGCAGATCTAG

TCAGAGCCTTGTACACAGTAATGGAAACACCTATTTACGTTGGTACCTGCAGAAGCCAGGCCAGTCTCCAAAGGTC

CTGATCTACAAAGTTTCCAACCGATTTTCTGGGGTCCCAGACAGGTTCAGTGGCAGTGGATCAGGGACAGATTTCA

CACTCAAGATCAGCAGAGTGGAGGCTGAGGATCTGGGAGTTTATTTCTGCTCTCAAAGTACACATGTTCCGTGGAC

GTTCGGTGGAGGCACCAAGCTGGAAATCAAA anti-FITC 4-4-2-(4420) VL aa

>SEQ ID: 38

DVVMTQTPLSLPVSLGDQASISCRSSQSLVHSNGNTYLRWYLQKPGQSPKVLIYKVSNRFSGVPDRFSGSGSGTDFT

LKISRVEAEDLGVYFCSQSTHVPWTFGGGTKLEIK anti-EGFRvlll mAb 806 VH nt

>SEQ ID: 39

GATGTGCAGCTTCAGGAGTCGGGACCTAGCCTGGTGAAACCTTCTCAGTCTCTGTCCCTCACCTGCACTGTCACTG

GCTACTCAATCACCAGTGATTTTGCCTGGAACTGGATTCGGCAGTTTCCAGGAAACAAGCTGGAGTGGATGGGCT

ACATAAGTTATAGTGGTAACACTAGGTACAACCCATCTCTCAAAAGTCGAATCTCTATCACTCGCGACACATCCAAG

AACCAATTCTTCCTGCAGTTGAACTCTGTGACTATTGAGGACACAGCCACATATTACTGTGTAACGGCGGGACGCG

GGTTTCCTTATTGGGGCCAAGGGACTCTGGTCACTGTCTCTGCA anti-EGFRvIII mAb 806 VH aa

>SEQ ID: 40

DVQLQESGPSLVKPSQSLSLTCTVTGYSITSDFAWNWIRQFPGNKLEWMGYISYSGNTRYNPSLKSRISITRDTSKN

QFFLQLNSVTIEDTATYYCVTAGRGFPYWGQGTLVTVSA anti-EGFRvlll mAb 806 VL nt

>SEQ ID: 41

GACATCCTGATGACCCAATCTCCATCCTCCATGTCTGTATCTCTGGGAGACACAGTCAGCATCACTTGCCATTCAAG

TCAGGACATTAACAGTAATATAGGGTGGTTGCAGCAGAGACCAGGGAAATCATTTAAGGGCCTGATCTATCATGG

AACCAACTTGGACGATGAAGTTCCATCAAGGTTCAGTGGCAGTGGATCTGGAGCCGATTATTCTCTCACCATCAGC

AGCCTGGAATCTGAAGATTTTGCAGACTATTACTGTGTACAGTATGCTCAGTTTCCGTGGACGTTCGGTGGAGGCA

CCAAGCTGGAAATCAAA anti-EGFRvllI mAb 806 VL aa

>SEQ ID: 42

DILMTQSPSSMSVSLGDTVSITCHSSQDINSNIGWLQQRPGKSFKGLIYHGTNLDDEVPSRFSGSGSGADYSLTISS

LESEDFADYYCVQYAQFPWTFGGGTKLEIK anti-CD19 21D4 VH nt

>SEQ ID: 43

GAGGTGCAGCTGGTGCAGTCTGGAGCAGAGGTGAAGAAACCAGGAGAGTCTCTGAAGATCTCCTGTAAGGGTTC

TGGATACAGCTTTAGCAGTTCATGGATCGGCTGGGTGCGCCAGGCACCTGGGAAAGGCCTGGAATGGATGGGGAT

CATCTATCCTGATGACTCTGATACCAGATACAGTCCATCCTTCCAAGGCCAGGTCACCATCTCAGCCGACAAGTC

-continued

CATCAGGACTGCCTACCTGCAGTGGAGTAGCCTGAAGGCCTCGGACACCGCTATGTATTACTGTGCGAGACATGT

TACTATGATTTGGGGAGTTATTATTGACTTCTGGGGCCAGGGAACCCTGGTCACCGTCTCCTCA anti-CD19 21D4 VH aa

>SEQ ID: 44

EVQLVQSGAEVKKPGESLKISCKGSGYSFSSSWIGWVRQAPGKGLEWMGIIYPDDSDTRYSPSFQGQVTISADKSIRTA

YLQWSSLKASDTAMYYCARHVTMIWGVIIDFWGQGTLVTVSS anti-CD19 21D4 VL nt

>SEQ ID: 45

GCCATCCAGTTGACCCAGTCTCCATCCTCCCTGTCTGCATCTGTAGGAGACAGAGTCACCATCACTTGCCGGGCAA

GTCAGGGCATTAGCAGTGCTTTAGCCTGGTATCAGCAGAAACCAGGGAAAGCTCCTAAGCTCCTGATCTATGATG

CCTCCAGTTTGGAAAGTGGGGTCCCATCAAGGTTCAGCGGCAGTGGATCTGGGACAGATTTCACTCTCACCATCAG

CAGCCTGCAGCCTGAAGATTTTGCAACTTATTACTGTCAACAGTTTAATAGTTACCCATTCACTTTCGGCCCTGGGA

CCAAAGTGGATATCAAA anti-CD19 21D4 VL aa

>SEQ ID: 46

AIQLTQSPSSLSASVGDRVTITCRASQGISSALAWYQQKPGKAPKLLIYDASSLESGVPSRFSGSGSGTDFTLTISSL

QPEDFATYYCQQFNSYPFTFGPGTKVDIK human IgG1 null (G1m-fa with ADCC/CDC null mutations) nt

>SEQ ID: 47

GCTAGCACCAAGGGCCCATCGGTCTTCCCCCTGGCACCCTCCTCCAAGAGCACCTCTGGGGGCACAGCGGCCCTG

GGCTGCCTGGTCAAGGACTACTTCCCCGAACCGGTGACGGTGTCGTGGAACTCAGGCGCCCTGACCAGCGGCGTG

CACACCTTCCCGGCTGTCCTACAGTCCTCAGGACTCTACTCCCTCAGCAGCGTGGTGACCGTGCCCTCCAGCAGCT

TGGGCACCCAGACCTACATCTGCAACGTGAATCACAAGCCCAGCAACACCAAGGTGGACAAGAGAGTTGAGCCCA

AATCTTGTGACAAAACTCACACATGCCCACCGTGCCCAGCACCTGAAGCCGCGGGGGCACCGTCAGTCTTCCTCTT

CCCCCCAAAACCCAAGGACACCCTCATGATCTCCCGGACCCCTGAGGTCACATGCGTGGTGGTGGACGTGAGCCA

CGAAGACCCTGAGGTCAAGTTCAACTGGTACGTGGACGGCGTGGAGGTGCATAATGCCAAGACAAAGCCGCGGG

AGGAGCAGTACAACAGCACGTACCGTGTGGTCAGCGTCCTCACCGTCCTGCACCAGGACTGGCTGAATGGCAAGG

AGTACAAGTGCGCGGTCTCCAACAAAGCCCTCCCAGCCCCCATCGAGAAAACCATCTCCAAAGCCAAAGGGCAGC

CCCGAGAACCACAGGTGTACACCCTGCCCCCATCCCGGGATGAGCTGACCAAGAACCAGGTCAGCCTGACCTGCC

TGGTCAAAGGCTTCTATCCCAGCGACATCGCCGTGGAGTGGGAGAGCAATGGGCAGCCGGAGAACAACTACAAG

ACCACGCCTCCCGTGCTGGACTCCGACGGCTCCTTCTTCCTCTATAGCAAGCTCACCGTGGACAAGAGCAGGTGGC

AGCAGGGGAACGTCTTCTCATGCTCCGTGATGCATGAGGCTCTGCACAACCACTACACGCAGAAGAGCCTCTCCCT

GTCTCCGGGT human IgG1 null (G1m-fa with ADCC/CDC null mutations) aa

>SEQ ID: 48

ASTKGPSVFPLAPSSKSTSGGTAALGCLVKDYFPEPVTVSWNSGALTSGVHTFPAVLQSSGLYSLSSVVTVPSSSLGTQTY

ICNVNHKPSNTKVDKRVEPKSCDKTHTCPPCPAPEAAGAPSVFLFPPKPKDTLMISRTPEVTCVVVDVSHEDPEVKFNW

YVDGVEVHNAKTKPREEQYNSTYRVVSVLTVLHQDWLNGKEYKCAVSNKALPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSVMHEALHN

HYTQKSLSLSPG human Ig Kappa nt

>SEQ ID: 49

CGTACGGTGGCTGCACCATCTGTCTTCATCTTCCCGCCATCTGATGAGCAGTTGAAATCTGGAACTGCCTCTGTTGT

GTGCCTGCTGAATAACTTCTATCCCAGAGAGGCCAAAGTACAGTGGAAGGTGGATAACGCCCTCCAATCGGGTAA

CTCCCAGGAGAGTGTCACAGAGCAGGACAGCAAGGACAGCACCTACAGCCTCAGCAGCACCCTGACGCTGAGCA

AAGCAGACTACGAGAAACACAAAGTCTACGCCTGCGAAGTCACCCATCAGGGCCTGAGCTCGCCCGTCACAAAGA

GCTTCAACAGGGGAGAGTGT

-continued human Ig Kappa aa

>SEQ ID: 50

RTVAAPSVFIFPPSDEQLKSGTASVVCLLNNFYPREAKVQWKVDNALQSGNSQESVTEQDSKDSTYSLSSTLTLSKADYE

KHKVYACEVTHQGLSSPVTKSFNRGEC

SI-27X63 (323H7-L1H4-scFv x PL230C6-H3-Fab x 284A10-H1L1-scFv) heavy chain nt

>SEQ ID: 51

GACATCCAGATGACCCAGTCTCCATCCTCCCTGTCTGCATCTGTAGGAGACAGAGTCACCATCACTTGCCAGTCCA

GTCAGAGTGTTTATAACAACAACGACTTAGCCTGGTATCAGCAGAAACCAGGGAAAGTTCCTAAGCTCCTGATCTA

TTATGCTTCCACTCTGGCATCTGGGGTCCCATCTCGGTTCAGTGGCAGTGGATCTGGGACAGATTTCACTCTCACCA

TCAGCAGCCTGCAGCCTGAAGATGTTGCAACTTATTACTGTGCAGGCGGTTATGATACGGATGGTCTTGATACGTT

TGCTTTCGGCGGAGGGACCAAGGTGGAGATCAAAGGCGGTGGCGGTAGTGGGGGAGGCGGTTCTGGCGGCGGA

GGGTCCGGCGGTGGAGGATCAGAGGTGCAGCTGTTGGAGTCTGGGGGAGGCTTGGTACAGCCTGGGGGGTCCC

TGAGACTCTCCTGTGCAGCCTCTGGATTCACCATCAGTCGCTACCACATGACTTGGGTCCGCCAGGCTCCAGGGAA

GGGGCTGGAGTGGATCGGACATATTTATGTTAATAATGATGACACAGACTACGCGAGCTCCGCGAAAGGCCGGTT

CACCATCTCCAGAGACAATTCCAAGAACACGCTGTATCTGCAAATGAACAGCCTGAGAGCCGAGGACACGGCCAC

CTATTTCTGTGCGAGATTGGATGTTGGTGGTGGTGGTGCTTATATTGGGGACATCTGGGGCCAGGGAACTCTGGT

TACCGTCTCTTCAGGCGGTGGAGGGTCCGGCGGTGGTGGATCCCAGTCGGTGGAGGAGTCTGGGGGAGGCTTGG

TCCAGCCTGGGGGGTCCCTGAGACTCTCCTGTACAGCCTCTGGAATCGACCTTAATACCTACGACATGATCTGGGT

CCGCCAGGCTCCAGGCAAGGGGCTAGAGTGGGTTGGAATCATTACTTATAGTGGTAGTAGATACTACGCGAACTG

GGCGAAAGGCCGATTCACCATCTCCAAAGACAATACCAAGAACACGGTGTATCTGCAAATGAACAGCCTGAGAGC

TGAGGACACGGCTGTGTATTACTGTGCCAGAGATTATATGAGTGGTTCCCACTTGTGGGGCCAGGGAACCCTGGT

CACCGTCTCTAGTGCTAGCACCAAGGGCCCATCGGTCTTCCCCCTGGCACCCTCCTCCAAGAGCACCTCTGGGGGC

ACAGCGGCCCTGGGCTGCCTGGTCAAGGACTACTTCCCCGAACCGGTGACGGTGTCGTGGAACTCAGGCGCCCTG

ACCAGCGGCGTGCACACCTTCCCGGCTGTCCTACAGTCCTCAGGACTCTACTCCCTCAGCAGCGTGGTGACCGTGC

CCTCCAGCAGCTTGGGCACCCAGACCTACATCTGCAACGTGAATCACAAGCCCAGCAACACCAAGGTGGACAAGA

GAGTTGAGCCCAAATCTTGTGACAAAACTCACACATGCCCACCGTGCCCAGCACCTGAAGCCGCGGGGGCACCGT

CAGTCTTCCTCTTCCCCCCAAAACCCAAGGACACCCTCATGATCTCCCGGACCCCTGAGGTCACATGCGTGGTGGT

GGACGTGAGCCACGAAGACCCTGAGGTCAAGTTCAACTGGTACGTGGACGGCGTGGAGGTGCATAATGCCAAGA

CAAAGCCGCGGGAGGAGCAGTACAACAGCACGTACCGTGTGGTCAGCGTCCTCACCGTCCTGCACCAGGACTGG

CTGAATGGCAAGGAGTACAAGTGCGCGGTCTCCAACAAAGCCCTCCCAGCCCCCATCGAGAAAACCATCTCCAAA

GCCAAAGGGCAGCCCCGAGAACCACAGGTGTATACCCTGCCCCCATCCCGGGATGAGCTGACCAAGAACCAGGTC

AGCCTGACCTGCCTGGTCAAAGGCTTCTATCCCAGCGACATCGCCGTGGAGTGGGAGAGCAATGGGCAGCCGGA

GAACAACTACAAGACCACGCCTCCCGTGCTGGACTCCGACGGCTCCTTCTTCCTCTATAGCAAGCTCACCGTGGAC

AAGAGCAGGTGGCAGCAGGGGAACGTCTTCTCATGCTCCGTGATGCATGAGGCTCTGCACAACCACTACACGCAG

AAGAGCCTCTCCCTGTCTCCGGGTGGCGGTGGAGGGTCCGGCGGTGGTGGATCCGAGGTGCAGCTGGTGGAGTC

TGGGGGAGGCTTGGTCCAGCCTGGGGGGTCCCTGAGACTCTCCTGTGCAGCCTCTGGATTCACCATCAGTACCAA

TGCAATGAGCTGGGTCCGCCAGGCTCCAGGGAAGGGGCTGGAGTGGATCGGAGTCATTACTGGTCGTGATATCA

CATACTACGCGAGCTGGGCGAAAGGCAGATTCACCATCTCCAGAGACAATTCCAAGAACACGCTGTATCTTCAAAT

GAACAGCCTGAGAGCCGAGGACACGGCTGTGTATTACTGTGCGCGCGACGGTGGATCATCTGCTATTACTAGTAA

CAACATTTGGGGCCAAGGAACTCTGGTCACCGTTTCTTCAGGCGGTGGCGGTAGTGGGGGAGGCGGTTCTGGCG

GCGGAGGGTCCGGCGGTGGAGGATCAGACGTCGTGATGACCCAGTCTCCTTCCACCCTGTCTGCATCTGTAGGAG

ACAGAGTCACCATCAATTGCCAAGCCAGTGAGAGCATTAGCAGTTGGTTAGCCTGGTATCAGCAGAAACCAGGGA

-continued

AAGCCCCTAAGCTCCTGATCTATGAAGCATCCAAACTGGCATCTGGGGTCCCATCAAGGTTCAGCGGCAGTGGATC

TGGGACAGAGTTCACTCTCACCATCAGCAGCCTGCAGCCTGATGATTTTGCAACTTATTACTGCCAAGGCTATTTTT

ATTTTATTAGTCGTACTTATGTAAATTCTTTCGGCGGAGGGACCAAGGTGGAGATCAAA

SI-27X63 (323H7-L1H4-scFv x PL230C6-H3-Fab x 284A10-H1L1-scFv) heavy chain aa >SEQ ID: 52

DIQMTQSPSSLSASVGDRVTITCQSSQSVYNNNDLAWYQQKPGKVPKLLIYYASTLASGVPSRFSGSGSGTDFTLTIS

SLQPEDVATYYCAGGYDTDGLDTFAFGGGTKVEIK (anti-ROR1 323H7 VLv1)

GGGGSGGGGSGGGGSGGGGS ($Gly_4Ser$)x4 linker

EVQLLESGGGLVQPGGSLRLSCAASGFTISRYHMTWVRQAPGKGLEWIGHIYVNNDDTDYASSAKGRFTISRDNSKNT

LYLQMNSLRAEDTATYFCARLDVGGGGAYIGDIWGQGTLVTVSS (anti-ROR1 323H7 VHv4)

GGGGSGGGGS ($Gly_4Ser$)x2 linker

QSVEESGGGLVQPGGSLRLSCTASGIDLNTYDMIWVRQAPGKGLEWVGIITYSGSRYYANWAKGRFTISKDNTKNTVY

LQMNSLRAEDTAVYYCARDYMSGSHLWGQGTLVTVSS (anti-PD-L1 PL230C6 VHv3)

ASTKGPSVFPLAPSSKSTSGGTAALGCLVKDYFPEPVTVSWNSGALTSGVHTFPAVLQSSGLYSLSSVVTVPSSSLGT

QTYICNVNHKPSNTKVDKRVEPKSCDKTHTCPPCPAPEAAGAPSVFLFPPKPKDTLMISRTPEVTCVVVDVSHEDPEV

KFNWYVDGVEVHNAKTKPREEQYNSTYRVVSVLTVLHQDWLNGKEYKCAVSNKALPAPIEKTISKAKGQPREPQVYTL

PPSRDELTKNQVSLTCLVKGFYPSDIAVEWESNGQPENNYKTTPPVLDSDGSFFLYSKLTVDKSRWQQGNVFSCSVMHE

ALHN

HYTQKSLSLSPG (human IgG1 null)

GGGGSGGGGS ($Gly_4Ser$)x2 linker

EVQLVESGGGLVQPGGSLRLSCAASGFTISTNAMSWVRQAPGKGLEWIGVITGRDITYYASWAKGRFTISRDNSKNTLY

LQMNSLRAEDTAVYYCARDGGSSAITSNNIWGQGTLVTVSS (anti-CD3 284A10 VHv1)

GGGGSGGGGSGGGGSGGGGS ($Gly_4Ser$)x4 linker

DVVMTQSPSTLSASVGDRVTINCQASESISSWLAWYQQKPGKAPKLLIYEASKLASGVPSRFSGSGSGTEFTLTISSLQ

PDDFATYYCQGYFYFISRTYVNSFGGGTKVEIK (anti-CD3 284A10 VLv1)

SI-27X63 (323H7-L1H4-scFv x PL230C6-H3-Fab x 284A10-H1L1-scFv) light chain nt >SEQ ID: 53

GCCTATGATATGACCCAGTCTCCATCTTCCGTGTCTGCATCTGTAGGAGACAGAGTCACCATCAAGTGTCAGGCCA

GTGAGGACATTTATAGCTTCTTGGCCTGGTATCAGCAGAAACCAGGGAAAGCCCCTAAGCTCCTGATCCATTCTGC

ATCCTCTCTGGCATCTGGGGTCCCATCAAGGTTCAGCGGCAGTGGATCTGGGACAGATTTCACTCTCACCATCAGC

AGCCTGCAGCCTGAAGATTTTGCAACTTACTATTGTCAACAGGGTTATGGTAAAAATAATGTTGATAATGCTTTCG

GCGGAGGGACCAAGGTGGAGATCAAACGTACGGTGGCTGCACCATCTGTCTTCATCTTCCCGCCATCTGATGAGC

AGTTGAAATCTGGAACTGCCTCTGTTGTGTGCCTGCTGAATAACTTCTATCCCAGAGAGGCCAAAGTACAGTGGAA

GGTGGATAACGCCCTCCAATCGGGTAACTCCCAGGAGAGTGTCACAGAGCAGGACAGCAAGGACAGCACCTACA

GCCTCAGCAGCACCCTGACGCTGAGCAAAGCAGACTACGAGAAACACAAAGTCTACGCCTGCGAAGTCACCCATC

AGGGCCTGAGCTCGCCCGTCACAAAGAGCTTCAACAGGGGAGAGTGT

SI-27X63 (323H7-L1H4-scFv x PL230C6-H3-Fab x 284A10-H1L1-scFv) light chain aa >SEQ ID: 54

AYDMTQSPSSVSASVGDRVTIKCQASEDIYSFLAWYQQKPGKAPKLLIHSASSLASGVPSRFSGSGSGTDFTLTISSLQPE

DFATYYCQQGYGKNNVDNAFGGGTKVEIK (anti-PD-L1 PL230C6 VLv2)

RTVAAPSVFIFPPSDEQLKSGTASVVCLLNNFYPREAKVQWKVDNALQSGNSQESVTEQDSKDSTYSLSSTLTLSKADYE

KHKVYACEVTHQGLSSPVTKSFNRGEC (human Ig Kappa)

What is claimed is:

1. A method for treating a cancer in a subject, said method comprising administering to the subject an effective amount of a pharmaceutical composition comprising a purified multi-specific antibody, wherein the multi-specific antibody comprises a tri-specific antibody monomer having a N-terminal and a C-terminal, comprising in tandem from the N-terminal to the C-terminal, a first scFv domain at the N-terminal, comprising the following pairs of amino acid sequences:

SEQ ID NOs: (2 and 4), (6 and 8), or (10 and 12), having the binding specificity against ROR1, SEQ ID NOs: (14 and 16), having the binding specificity against PD-L1, SEQ ID NOs: (40 and 42), having the binding specificity against EGFRvIII, or SEQ ID NOs: (44 and 46), having the binding specificity against CD19, a Fab domain, having a binding specificity against PD-L1, EGFRvIII, or CD19, a Fc domain, and a second scFv domain at the C-terminal, having a binding specificity against CD3 and comprising the following pairs of sequences SEQ ID NOs: (18 and 20), (22 and 24), (26 and 28), (30 and 32), or (30 and 34), wherein the first scFv domain, the Fab domain, and the second scFv domain each has a binding specificity against a different antigen, and wherein the cancer comprises cells expressing ROR1, PD-L1, EGFRvIII, or CD19.

2. The method of claim 1, further comprising co-administering an effective amount of a therapeutic agent.

3. The method of claim 2, wherein the therapeutic agent comprises an anti-estrogen agent, a receptor tyrosine kinase inhibitor, a kinase inhibitor, a cell cycle inhibitor, a DNA, RNA or protein synthesis inhibitor, a RAS inhibitor, a check point inhibitor, an inhibitor of PD1, PDL1, CTLA4, 4-1BB, OX40, GITR, ICOS, LIGHT, TIM3, LAG3, TIGIT, CD40, CD27, HVEM, BTLA, VISTA, B7H4, CSF1R, NKG2D, CD73, a derivative or a combination thereof.

4. The method of claim 1, wherein the first scFv domain the has a binding specificity against EGFRvIII and comprises 3 CDRs of SEQ ID NO:40 and 3 CDRs of SEQ ID NO:42, wherein the first scFv domain has a binding specificity against CD19 and comprises 3 CDRs of SEQ ID NO:44 and 3 CDRs of SEQ ID NO:46, or wherein the first scFv domain has a binding specificity against PD-L1 and comprises 3 CDRs of SEQ ID NO: 14 and 3 CDRs of SEQ ID NO: 16.

5. The method of claim 1, wherein the first scFv domain, the Fab domain, and the second scFv domain each independently has a binding specificity against an antigen selected from ROR1, PD-L1, and CD3.

6. The method of claim 1, wherein the first scFv domain has a binding specificity against ROR1, and wherein the first scFv comprises 3 complementarity determining regions (CDRs) of SEQ ID NO:6 and 3 CDRs of SEQ ID NO:8.

7. The method of claim 1, wherein the Fab domain has a binding specificity against PD-L1.

8. The method of claim 1, wherein the second scFv domain has a binding specificity against CD3, and wherein the second scFv comprises 3 CDRs of SEQ ID NO: 22 and 3 CDRs of SEQ ID NO:24.

9. The method of claim 1, wherein the first scFv domain has a binding specificity against PD-L1, and wherein the first scFv comprises 3 CDRs of SEQ ID NO: 14 and 3 CDRs of SEQ ID NO: 16.

10. The method of claim 1, wherein the Fc domain comprises SEQ ID NO: 48 or 50.

11. The method of claim 1, wherein the tri-specific antibody monomer has a binding specificity to human PD-L1, human CD3, and one of human ROR1, human CD19, or EGFR VIII.

12. The method of claim 1, wherein the first scFv domain comprises a $(G4S)_n$ linker, wherein n is an integral from 2 to 4 and wherein the first scFv domain is linked to the Fab domain through the linker.

13. The method of claim 1, wherein the tri-specific antibody monomer comprises a binding domain having a binding specificity to human ROR1, wherein the binding domain comprises a pair of amino acid sequences selected from SEQ ID: 2 and 4, SEQ ID: 6 and 8, and SEQ ID: 10 and 12.

14. The method of claim 1, wherein the tri-specific antibody monomer comprises a binding domain having a binding specificity to human CD19, wherein the binding domain comprises a pair of amino acid sequences of SEQ ID: 44 and 46.

15. The method of claim 1, wherein the tri-specific antibody monomer comprises a binding domain having a binding specificity to EGFR vIII, wherein the binding domain comprises a pair of amino acid sequences of SEQ ID: 40 and 42.

16. The method of claim 1, wherein the tri-specific antibody monomer comprises a binding domain having a binding specificity to human PD-L1, wherein the binding domain comprises a pair of amino acid sequences of SEQ ID: 14 and 16.

17. A method for treating a cancer that comprises cells expressing ROR1, PD-L1, EGFRvIII, or CD19 in a subject, said method comprising administering to the subject an effective amount of a pharmaceutical composition comprising a tri-specific antibody having a N-terminal and a C-terminal, comprising in tandem from the N-terminal to the C-terminal, a first scFv domain at the N-terminal, a Fab domain, a Fc domain, and a second scFv domain at the C-terminal, comprising 3 CDRs of SEQ ID NO: 22 and 3 CDRs of SEQ ID NO: 24, wherein the tri-specific antibody comprises 3 CDRs of SEQ ID NO: 14 and 3 CDRs of SEQ ID NO: 16, and one of:

3 CDRs of SEQ ID NO: 6 and 3 CDRs of SEQ ID NO: 8,

3 CDRs of SEQ ID NO: 40 and 3 CDRs of SEQ ID NO: 42, and

3 CDRs of SEQ ID NO: 44 and 3 CDRs of SEQ ID NO: 46.

18. The method of claim 17, wherein the tri-specific antibody has a binding specificity to PD-L1, CD3, and one of ROR1, CD19 and EGFRvIII.

* * * * *

SEQUENCE LISTING

```
Sequence total quantity: 54
SEQ ID NO: 1            moltype = DNA  length = 348
FEATURE                 Location/Qualifiers
misc_feature            1..348
                        note = synthesized
source                  1..348
                        mol_type = other DNA
                        organism = synthetic construct
SEQUENCE: 1
cagtccgtga aggagtccga gggcgacctg gtgacccccg ccggcaacct gaccctgacc  60
tgcaccgcct ccggctccga catcaacgac taccccatct cctgggtgcg gcaggccccc  120
ggcaagggcc tggagtggat cggcttcatc aactccggcg gctccacctg gtacgcctcc  180
tgggtgaagg gccggttcac catctcccgg acctccacca ccgtggacct gaagatgacc  240
tccctgacca ccgacgacac cgccacctac ttctgcgccc ggggctactc cacctactac  300
ggcgacttca acatctgggg ccccggcacc ctggtgacca tctcctcg               348

SEQ ID NO: 2            moltype = AA  length = 116
FEATURE                 Location/Qualifiers
REGION                  1..116
                        note = synthesized
source                  1..116
                        mol_type = protein
                        organism = synthetic construct
SEQUENCE: 2
QSVKESEGDL VTPAGNLTLT CTASGSDIND YPISWVRQAP GKGLEWIGFI NSGGSTWYAS  60
WVKGRFTISR TSTTVDLKMT SLTTDDTATY FCARGYSTYY GDFNIWGPGT LVTISS      116

SEQ ID NO: 3            moltype = DNA  length = 330
FEATURE                 Location/Qualifiers
misc_feature            1..330
                        note = synthesized
source                  1..330
                        mol_type = other DNA
                        organism = synthetic construct
SEQUENCE: 3
gagctggtga tgacccagac cccctcctcc acctccggcg ccgtgggcgg caccgtgacc  60
atcaactgcc aggcctccca gtccatcgac tccaacctgg cctggttcca gcagaagccc  120
ggccagcccc ccaccctgct gatctaccgg gcctccaacc tggcctccgg cgtgccctcc  180
cggttctccg gctcccggtc cggcaccgag tacaccctga ccatctccgg cgtgcagcgg  240
gaggacgccg ccacctacta ctgcctgggc ggcgtgggca acgtgtccta ccggacctcc  300
ttcggcggcg gcaccgaggt ggtggtgaag                                   330

SEQ ID NO: 4            moltype = AA  length = 110
FEATURE                 Location/Qualifiers
REGION                  1..110
                        note = synthesized
source                  1..110
                        mol_type = protein
                        organism = synthetic construct
SEQUENCE: 4
ELVMTQTPSS TSGAVGGTVT INCQASQSID SNLAWFQQKP GQPPTLLIYR ASNLASGVPS  60
RFSGSRSGTE YTLTISGVQR EDAATYYCLG GVGNVSYRTS FGGGTEVVVK            110

SEQ ID NO: 5            moltype = DNA  length = 366
FEATURE                 Location/Qualifiers
misc_feature            1..366
                        note = synthesized
source                  1..366
                        mol_type = other DNA
                        organism = synthetic construct
SEQUENCE: 5
gaggtgcagc tgttggagtc tgggggaggc ttggtacagc ctggggggtc cctgagactc  60
tcctgtgcag cctctggatt caccatcagt cgctaccaca tgacttgggt ccgccaggct  120
ccagggaagg ggctggagtg gatcggacat atttatgtta ataatgatga cacagactac  180
gcgagctccg cgaaaggccg gttcaccatc tccagagaca attccaagaa cacgctgtat  240
ctgcaaatga acagcctgag agccgaggac acggccacct atttctgtgc gagattggat  300
gttggtggtg gtggtgctta tattggggac atctggggcc agggaactct ggttaccgtc  360
tcttca                                                             366

SEQ ID NO: 6            moltype = AA  length = 122
FEATURE                 Location/Qualifiers
REGION                  1..122
                        note = synthesized
source                  1..122
                        mol_type = protein
                        organism = synthetic construct
SEQUENCE: 6
EVQLLESGGG LVQPGGSLRL SCAASGFTIS RYHMTWVRQA PGKGLEWIGH IYVNNDDTDY  60
```

-continued

```
ASSAKGRFTI SRDNSKNTLY LQMNSLRAED TATYFCARLD VGGGGAYIGD IWGQGTLVTV  120
SS                                                                122

SEQ ID NO: 7            moltype = DNA  length = 339
FEATURE                 Location/Qualifiers
misc_feature            1..339
                        note = synthesized
source                  1..339
                        mol_type = other DNA
                        organism = synthetic construct
SEQUENCE: 7
gacatccaga tgacccagtc tccatcctcc ctgtctgcat ctgtaggaga cagagtcacc  60
atcacttgcc agtccagtca gagtgtttat aacaacaacg acttagcctg gtatcagcag  120
aaaccaggga aagttcctaa gctcctgatc tattatgctt ccactctggc atctggggtc  180
ccatctcggt tcagtggcag tggatctggg acagatttca ctctcaccat cagcagcctg  240
cagcctgaag atgttgcaac ttattactgt gcaggcggtt atgatacgga tggtcttgat  300
acgtttgctt tcggcggagg gaccaaggtg gagatcaaa                        339

SEQ ID NO: 8            moltype = AA  length = 113
FEATURE                 Location/Qualifiers
REGION                  1..113
                        note = synthesized
source                  1..113
                        mol_type = protein
                        organism = synthetic construct
SEQUENCE: 8
DIQMTQSPSS LSASVGDRVT ITCQSSQSVY NNNDLAWYQQ KPGKVPKLLI YYASTLASGV  60
PSRFSGSGSG TDFTLTISSL QPEDVATYYC AGGYDTDGLD TFAFGGGTKV EIK        113

SEQ ID NO: 9            moltype = DNA  length = 345
FEATURE                 Location/Qualifiers
misc_feature            1..345
                        note = synthesized
source                  1..345
                        mol_type = other DNA
                        organism = synthetic construct
SEQUENCE: 9
gaggtgcagc tggtggagtc tgggggaggc ttggtccagc ctgggggggtc cctgagactc  60
tcctgtactg cctctggatt ctccctcagt agctatgcaa tgagctgggt ccgccaggct  120
ccagggaggg ggctggagtg gatcggaatc atttatgcta gtggtagcac atactacgcg  180
agctcggcga aaggcagatt caccatctcc aaagacaata ccaagaacac ggtggatctt  240
caaatgaaca gcctgagagc cgaggacacg gctgtgtatt actgtgcgag aatttatgac  300
ggcatggacc tctggggcca gggaactctg gttaccgtct cttca                 345

SEQ ID NO: 10           moltype = AA  length = 115
FEATURE                 Location/Qualifiers
REGION                  1..115
                        note = synthesized
source                  1..115
                        mol_type = protein
                        organism = synthetic construct
SEQUENCE: 10
EVQLVESGGG LVQPGGSLRL SCTASGFSLS SYAMSWVRQA PGRGLEWIGI IYASGSTYYA  60
SSAKGRFTIS KDNTKNTVDL QMNSLRAEDT AVYYCARIYD GMDLWGQGTL VTVSS       115

SEQ ID NO: 11           moltype = DNA  length = 321
FEATURE                 Location/Qualifiers
misc_feature            1..321
                        note = synthesized
source                  1..321
                        mol_type = other DNA
                        organism = synthetic construct
SEQUENCE: 11
gacatccaga tgacccagtc tccatcctcc ctgtctgcat ctgtaggaga cagagtcacc  60
atcaattgcc aggccagtca gaacatttac agctacttat cctggtatca gcagaaacca  120
gggaaagttc ctaagcgcct gatctatctg gcatctactc tggcatctgg ggtcccatct  180
cggttcagtg gcagtggatc tgggacagat tacactctca ccatcagcag cctgcagcct  240
gaagatgttg caacttatta ctgtcaaagc aattataacg gtaattatgg tttcggcgga  300
gggaccaagg tggagatcaa a                                           321

SEQ ID NO: 12           moltype = AA  length = 107
FEATURE                 Location/Qualifiers
REGION                  1..107
                        note = synthesized
source                  1..107
                        mol_type = protein
                        organism = synthetic construct
SEQUENCE: 12
DIQMTQSPSS LSASVGDRVT INCQASQNIY SYLSWYQQKP GKVPKRLIYL ASTLASGVPS  60
```

```
RFSGSGSGTD YTLTISSLQP EDVATYYCQS NYNGNYGFGG GTKVEIK              107

SEQ ID NO: 13          moltype = DNA  length = 345
FEATURE                Location/Qualifiers
misc_feature           1..345
                       note = synthesized
source                 1..345
                       mol_type = other DNA
                       organism = synthetic construct
SEQUENCE: 13
cagtcggtgg aggagtctgg gggaggcttg gtccagcctg gggggtccct gagactctcc  60
tgtacagcct ctggaatcga ccttaatacc tacgacatga tctgggtccg ccaggctcca  120
ggcaaggggc tagagtgggt tggaatcatt acttatagtg gtagtagata ctacgcgaac  180
tgggcgaaag gccgattcac catctccaaa gacaatacca agaacacggt gtatctgcaa  240
atgaacagcc tgagagctga ggacacggct gtgtattact gtgccagaga ttatatgagt  300
ggttcccact tgtggggcca gggaaccctg gtcaccgtct ctagt                  345

SEQ ID NO: 14          moltype = AA  length = 115
FEATURE                Location/Qualifiers
REGION                 1..115
                       note = synthesized
source                 1..115
                       mol_type = protein
                       organism = synthetic construct
SEQUENCE: 14
QSVEESGGGL VQPGGSLRLS CTASGIDLNT YDMIWVRQAP GKGLEWVGII TYSGSRYYAN  60
WAKGRFTISK DNTKNTVYLQ MNSLRAEDTA VYYCARDYMS GSHLWGQGTL VTVSS       115

SEQ ID NO: 15          moltype = DNA  length = 330
FEATURE                Location/Qualifiers
misc_feature           1..330
                       note = synthesized
source                 1..330
                       mol_type = other DNA
                       organism = synthetic construct
SEQUENCE: 15
gcctatgata tgacccagtc tccatcttcc gtgtctgcat ctgtaggaga cagagtcacc  60
atcaagtgtc aggccagtga ggacatttat agcttcttgg cctggtatca gcagaaacca  120
gggaaagccc ctaagctcct gatccattct gcatcctctc tggcatctgg ggtcccatca  180
aggttcagcg gcagtggatc tgggacagat ttcactctca ccatcagcag cctgcagcct  240
gaagattttg caacttacta ttgtcaacag ggttatggta aaaataatgt tgataatgct  300
ttcggcggag ggaccaaggt ggagatcaaa                                   330

SEQ ID NO: 16          moltype = AA  length = 110
FEATURE                Location/Qualifiers
REGION                 1..110
                       note = synthesized
source                 1..110
                       mol_type = protein
                       organism = synthetic construct
SEQUENCE: 16
AYDMTQSPSS VSASVGDRVT IKCQASEDIY SFLAWYQQKP GKAPKLLIHS ASSLASGVPS  60
RFSGSGSGTD FTLTISSLQP EDFATYYCQQ GYGKNNVDNA FGGGTKVEIK            110

SEQ ID NO: 17          moltype = DNA  length = 375
FEATURE                Location/Qualifiers
misc_feature           1..375
                       note = synthesized
source                 1..375
                       mol_type = other DNA
                       organism = synthetic construct
SEQUENCE: 17
caggtgcaat tggtggaaag cggaggggga ctggtgcagc ccgggggaag tctgaagctg  60
tcctgtgccg ccagcggctt taccttcaac aagtacgcca tgaattgggt ccgacaggcc  120
ccagggaaag gcctggaatg ggtggcacgg attcggtcca agtacaacaa ctacgccacc  180
tactacgctg actccgtgaa ggacagattc accatcagcc gggacgactc taagaacacc  240
gcctatctgc agatgaacaa cctgaaaacc gaggatacag ctgtgtacta ttgtgtgcgg  300
cacggcaact tcggcaactc ctacatctcc tactgggcct attggggaca gggaacactg  360
gtcaccgtgt ctagc                                                   375

SEQ ID NO: 18          moltype = AA  length = 125
FEATURE                Location/Qualifiers
REGION                 1..125
                       note = synthesized
source                 1..125
                       mol_type = protein
                       organism = synthetic construct
SEQUENCE: 18
QVQLVESGGG LVQPGGSLKL SCAASGFTFN KYAMNWVRQA PGKGLEWVAR IRSKYNNYAT  60
```

```
YYADSVKDRF TISRDDSKNT AYLQMNNLKT EDTAVYYCVR HGNFGNSYIS YWAYWGQGTL  120
VTVSS                                                             125

SEQ ID NO: 19           moltype = DNA  length = 333
FEATURE                 Location/Qualifiers
misc_feature            1..333
                        note = synthesized
source                  1..333
                        mol_type = other DNA
                        organism = synthetic construct
SEQUENCE: 19
cagaccgtgg tcacccagga accttccctg accgtctccc caggcggcac cgtgaccctg  60
acctgtggct cctctaccgg cgctgtgacc tccggcaact accctaactg ggtgcagcag  120
aaacccggac aggctcctag aggcctgatc ggcggcacca agtttctggc ccctggcacc  180
cctgccagat tctccggctc cctgctggga ggcaaggccg ctctgaccct gtctggcgtg  240
cagcctgagg acgaggccga gtactactgt gtgctgtggt actccaacag atgggtgttc  300
ggaggcggca caaagctgac cgtgctgtcc tcg                               333

SEQ ID NO: 20           moltype = AA  length = 111
FEATURE                 Location/Qualifiers
REGION                  1..111
                        note = synthesized
source                  1..111
                        mol_type = protein
                        organism = synthetic construct
SEQUENCE: 20
QTVVTQEPSL TVSPGGTVTL TCGSSTGAVT SGNYPNWVQQ KPGQAPRGLI GGTKFLAPGT  60
PARFSGSLLG GKAALTLSGV QPEDEAEYYC VLWYSNRWVF GGGTKLTVLS S           111

SEQ ID NO: 21           moltype = DNA  length = 360
FEATURE                 Location/Qualifiers
misc_feature            1..360
                        note = synthesized
source                  1..360
                        mol_type = other DNA
                        organism = synthetic construct
SEQUENCE: 21
gaggtgcagc tggtggagtc tggggggaggc ttggtccagc ctggggggtc cctgagactc  60
tcctgtgcag cctctggatt caccatcagt accaatgcaa tgagctgggt ccgccaggct  120
ccagggaagg ggctggagtg gatcggagtc attactggtc gtgatatcac atactacgcg  180
agctgggcga aaggcagatt caccatctcc agagacaatt ccaagaacac gctgtatctt  240
caaatgaaca gcctgagagc cgaggacacg gctgtgtatt actgtgcgcg cgacggtgga  300
tcatctgcta ttactagtaa caacatttgg ggccaaggaa ctctggtcac cgtttcttca  360

SEQ ID NO: 22           moltype = AA  length = 120
FEATURE                 Location/Qualifiers
REGION                  1..120
                        note = synthesized
source                  1..120
                        mol_type = protein
                        organism = synthetic construct
SEQUENCE: 22
EVQLVESGGG LVQPGGSLRL SCAASGFTIS TNAMSWVRQA PGKGLEWIGV ITGRDITYYA  60
SWAKGRFTIS RDNSKNTLYL QMNSLRAEDT AVYYCARDGG SSAITSNNIW GQGTLVTVSS  120

SEQ ID NO: 23           moltype = DNA  length = 336
FEATURE                 Location/Qualifiers
misc_feature            1..336
                        note = synthesized
source                  1..336
                        mol_type = other DNA
                        organism = synthetic construct
SEQUENCE: 23
gacgtcgtga tgacccagtc tccttccacc ctgtctgcat ctgtaggaga cagagtcacc  60
atcaattgcc aagccagtga gagcattagc agttggttag cctggtatca gcagaaacca  120
gggaaagccc ctaagctcct gatctatgaa gcatccaaac tggcatctgg ggtcccatca  180
aggttcagcg gcagtggatc tgggacagag ttcactctca ccatcagcag cctgcagcct  240
gatgattttg caacttatta ctgccaaggc tatttttatt ttattagtcg tacttatgta  300
aattctttcg gcggagggac caaggtggag atcaaa                            336

SEQ ID NO: 24           moltype = AA  length = 112
FEATURE                 Location/Qualifiers
REGION                  1..112
                        note = synthesized
source                  1..112
                        mol_type = protein
                        organism = synthetic construct
SEQUENCE: 24
DVVMTQSPST LSASVGDRVT INCQASESIS SWLAWYQQKP GKAPKLLIYE ASKLASGVPS  60
```

```
RFSGSGSGTE FTLTISSLQP DDFATYYCQG YFYFISRTYV NSFGGGTKVE IK          112

SEQ ID NO: 25          moltype = DNA  length = 360
FEATURE                Location/Qualifiers
misc_feature           1..360
                       note = synthesized
source                 1..360
                       mol_type = other DNA
                       organism = synthetic construct
SEQUENCE: 25
gaggtgcagc tggtggagtc tgggggaggc ttggtccagc ctgggggtc cctgagactc  60
tcctgtacgg cctctggatt caccatcagt agcaatgcaa tgagctgggt ccgccaggct  120
ccagggaagg ggctggagtg gatcggagtc attactggtc gtgatatcac atactacgcg  180
agctgggcga aaggcagatt caccatctcc aaagacacct ccaagaacac ggtggatctt  240
caaatgaaca gcctgagagc cgaggacacg gctgtgtatt actgtgcgcg cgacggtgga  300
tcatctgcta ttactagtaa caacatttgg ggccaaggaa ctctggtcac cgtttcttca  360

SEQ ID NO: 26          moltype = AA  length = 120
FEATURE                Location/Qualifiers
REGION                 1..120
                       note = synthesized
source                 1..120
                       mol_type = protein
                       organism = synthetic construct
SEQUENCE: 26
EVQLVESGGG LVQPGGSLRL SCTASGFTIS SNAMSWVRQA PGKGLEWIGV ITGRDITYYA  60
SWAKGRFTIS KDTSKNTVDL QMNSLRAEDT AVYYCARDGG SSAITSNNIW GQGTLVTVSS  120

SEQ ID NO: 27          moltype = DNA  length = 336
FEATURE                Location/Qualifiers
misc_feature           1..336
                       note = synthesized
source                 1..336
                       mol_type = other DNA
                       organism = synthetic construct
SEQUENCE: 27
gacatccaga tgacccagtc tccttccacc ctgtctgcat ctgtaggaga cagagtcacc  60
atcacttgcc aagccagtga gagcattagc agttggttag cctggtatca gcagaaacca  120
gggaaagccc ctaagctcct gatctatgaa gcatccaaac tggcatctgg ggtcccatca  180
aggttcagcg gcagtggatc tgggacagag ttcactctca ccatcagcag cctgcagcct  240
gatgattttg caacttatta ctgccaaggc tatttttatt ttattagtcg tagttatgta  300
aatgctttcg gcggagggac caaggtggag atcaaa                           336

SEQ ID NO: 28          moltype = AA  length = 112
FEATURE                Location/Qualifiers
REGION                 1..112
                       note = synthesized
source                 1..112
                       mol_type = protein
                       organism = synthetic construct
SEQUENCE: 28
DIQMTQSPST LSASVGDRVT ITCQASESIS SWLAWYQQKP GKAPKLLIYE ASKLASGVPS  60
RFSGSGSGTE FTLTISSLQP DDFATYYCQG YFYFISRSYV NAFGGGTKVE IK          112

SEQ ID NO: 29          moltype = DNA  length = 360
FEATURE                Location/Qualifiers
misc_feature           1..360
                       note = synthesized
source                 1..360
                       mol_type = other DNA
                       organism = synthetic construct
SEQUENCE: 29
gaggtgcagc tggtggagtc tgggggaggc ttggtccagc ctgggggtc cctgagactc  60
tcctgtgcag cctctggaat cgacctcagt agcaatgcaa tgagctgggt ccgccaggct  120
ccagggaagg ggctggagtg gatcggagtc attactggtc gtgatatcac atactacgcg  180
agctgggcga aaggcagatt caccatctcc agagacaatt ccaagaacac gctgtatctt  240
caaatgaaca gcctgagagc cgaggacacg gctgtgtatt actgtgcgcg cgacggtgga  300
tcatctgcta ttaatagtaa gaacatttgg ggccaaggaa ctctggtcac cgtttcttca  360

SEQ ID NO: 30          moltype = AA  length = 120
FEATURE                Location/Qualifiers
REGION                 1..120
                       note = synthesized
source                 1..120
                       mol_type = protein
                       organism = synthetic construct
SEQUENCE: 30
EVQLVESGGG LVQPGGSLRL SCAASGIDLS SNAMSWVRQA PGKGLEWIGV ITGRDITYYA  60
SWAKGRFTIS RDNSKNTLYL QMNSLRAEDT AVYYCARDGG SSAINSKNIW GQGTLVTVSS  120
```

```
SEQ ID NO: 31          moltype = DNA  length = 360
FEATURE                Location/Qualifiers
misc_feature           1..360
                       note = synthesized
source                 1..360
                       mol_type = other DNA
                       organism = synthetic construct
SEQUENCE: 31
gaggtgcagc tggtggagtc tgggggaggc ttggtccagc ctggagggtc cctgagactc  60
tcctgtacgg cctctggaat cgacctcagt agcaatgcaa tgagctgggt ccgccaggct  120
ccagggaaag ggctggagtg gatcggagtc attactggtc gtgatatcac atactacgcg  180
agctgggcga aaggcagatt caccatctcc aaagacacct ccaagaacac ggtggatctt  240
caaatgaaca gcctgagagc cgaggacacg gctgtgtatt actgtgcgcg cgacggtgga  300
tcatctgcta ttaatagtaa gaacatttgg ggccaaggaa ctctggtcac cgtttcttca  360

SEQ ID NO: 32          moltype = AA  length = 120
FEATURE                Location/Qualifiers
REGION                 1..120
                       note = synthesized
source                 1..120
                       mol_type = protein
                       organism = synthetic construct
SEQUENCE: 32
EVQLVESGGG LVQPGGSLRL SCTASGIDLS SNAMSWVRQA PGKGLEWIGV ITGRDITYYA  60
SWAKGRFTIS KDTSKNTVDL QMNSLRAEDT AVYYCARDGG SSAINSKNIW GQGTLVTVSS  120

SEQ ID NO: 33          moltype = DNA  length = 336
FEATURE                Location/Qualifiers
misc_feature           1..336
                       note = synthesized
source                 1..336
                       mol_type = other DNA
                       organism = synthetic construct
SEQUENCE: 33
gacatccaga tgacccagtc tccttccacc ctgtctgcat ctgtaggaga cagagtcacc  60
atcacttgcc aagccagtga gagcattagc agttggttag cctggtatca gcagaaacca  120
gggaaagccc ctaagctcct gatctatgaa gcatccaaac tggcatctgg ggtcccatca  180
aggttcagcg gcagtggatc tgggacagag ttcactctca ccatcagcag cctgcagcct  240
gatgattttg caacttatta ctgccaaggc tatttttatt ttattagtcg tacttatgta  300
aatgctttcg gcggagggac caaggtggag atcaaa                             336

SEQ ID NO: 34          moltype = AA  length = 112
FEATURE                Location/Qualifiers
REGION                 1..112
                       note = synthesized
source                 1..112
                       mol_type = protein
                       organism = synthetic construct
SEQUENCE: 34
DIQMTQSPST LSASVGDRVT ITCQASESIS SWLAWYQQKP GKAPKLLIYE ASKLASGVPS  60
RFSGSGSGTE FTLTISSLQP DDFATYYCQG YFYFISRTYV NAFGGGTKVE IK          112

SEQ ID NO: 35          moltype = DNA  length = 354
FEATURE                Location/Qualifiers
misc_feature           1..354
                       note = synthesized
source                 1..354
                       mol_type = other DNA
                       organism = synthetic construct
SEQUENCE: 35
gaggtgaagc tggatgagac tggaggaggc ttggtgcaac ctgggaggcc catgaaactc  60
tcctgtgttg cctctggatt cacttttagt gactactgga tgaactgggt ccgccagtct  120
ccagagaaag gactggagtg ggtagcacaa attagaaaca aaccttataa ttatgaaaca  180
tattattcag attctgtgaa aggcagattc accatctcaa gagatgattc caaaagtagt  240
gtctacctgc aaatgaacaa cttaagagtt gaagacatgg gtatctatta ctgtacgggt  300
tcttactatg gtatggacta ctggggtcaa ggaacctcag tcaccgtctc ctca        354

SEQ ID NO: 36          moltype = AA  length = 118
FEATURE                Location/Qualifiers
REGION                 1..118
                       note = synthesized
source                 1..118
                       mol_type = protein
                       organism = synthetic construct
SEQUENCE: 36
EVKLDETGGG LVQPGRPMKL SCVASGFTFS DYWMNWVRQS PEKGLEWVAQ IRNKPYNYET  60
YYSDSVKGRF TISRDDSKSS VYLQMNNLRV EDMGIYYCTG SYYGMDYWGQ GTSVTVSS    118
```

```
SEQ ID NO: 37          moltype = DNA  length = 336
FEATURE                Location/Qualifiers
misc_feature           1..336
                       note = synthesized
source                 1..336
                       mol_type = other DNA
                       organism = synthetic construct
SEQUENCE: 37
gatgtcgtga tgacccaaac tccactctcc ctgcctgtca gtcttggaga tcaagcctcc  60
atctcttgca gatctagtca gagccttgta cacagtaatg gaaacaccta tttacgttgg  120
tacctgcaga agccaggcca gtctccaaag gtcctgatct acaaagtttc caaccgattt  180
tctggggtcc cagacaggtt cagtggcagt ggatcaggga cagatttcac actcaagatc  240
agcagagtgg aggctgagga tctgggagtt tatttctgct ctcaaagtac acatgttccg  300
tggacgttcg gtggaggcac caagctggaa atcaaa                            336

SEQ ID NO: 38          moltype = AA  length = 112
FEATURE                Location/Qualifiers
REGION                 1..112
                       note = synthesized
source                 1..112
                       mol_type = protein
                       organism = synthetic construct
SEQUENCE: 38
DVVMTQTPLS LPVSLGDQAS ISCRSSQSLV HSNGNTYLRW YLQKPGQSPK VLIYKVSNRF  60
SGVPDRFSGS GSGTDFTLKI SRVEAEDLGV YFCSQSTHVP WTFGGGTKLE IK          112

SEQ ID NO: 39          moltype = DNA  length = 348
FEATURE                Location/Qualifiers
misc_feature           1..348
                       note = synthesized
source                 1..348
                       mol_type = other DNA
                       organism = synthetic construct
SEQUENCE: 39
gatgtgcagc ttcaggagtc gggacctagc ctggtgaaac cttctcagtc tctgtccctc  60
acctgcactg tcactggcta ctcaatcacc agtgattttg cctggaactg gattcggcag  120
tttccaggaa acaagctgga gtggatgggc tacataagtt atagtggtaa cactaggtac  180
aacccatctc tcaaaagtcg aatctctatc actcgcgaca catccaagaa ccaattcttc  240
ctgcagttga actctgtgac tattgaggac acagccacat attactgtgt aacggcggga  300
cgcgggtttc cttattgggg ccaagggact ctggtcactg tctctgca                348

SEQ ID NO: 40          moltype = AA  length = 116
FEATURE                Location/Qualifiers
REGION                 1..116
                       note = synthesized
source                 1..116
                       mol_type = protein
                       organism = synthetic construct
SEQUENCE: 40
DVQLQESGPS LVKPSQSLSL TCTVTGYSIT SDFAWNWIRQ FPGNKLEWMG YISYSGNTRY  60
NPSLKSRISI TRDTSKNQFF LQLNSVTIED TATYYCVTAG RGFPYWGQGT LVTVSA      116

SEQ ID NO: 41          moltype = DNA  length = 321
FEATURE                Location/Qualifiers
misc_feature           1..321
                       note = synthesized
source                 1..321
                       mol_type = other DNA
                       organism = synthetic construct
SEQUENCE: 41
gacatcctga tgacccaatc tccatcctcc atgtctgtat ctctgggaga cacagtcagc  60
atcacttgcc attcaagtca ggacattaac agtaatatag ggtggttgca gcagagacca  120
gggaaatcat ttaagggcct gatctatcat ggaaccaact tggacgatga agttccatca  180
aggttcagtg gcagtggatc tggagccgat tattctctca ccatcagcag cctggaatct  240
gaagattttg cagactatta ctgtgtacag tatgctcagt ttccgtggac gttcggtgga  300
ggcaccaagc tggaaatcaa a                                            321

SEQ ID NO: 42          moltype = AA  length = 107
FEATURE                Location/Qualifiers
REGION                 1..107
                       note = synthesized
source                 1..107
                       mol_type = protein
                       organism = synthetic construct
SEQUENCE: 42
DILMTQSPSS MSVSLGDTVS ITCHSSQDIN SNIGWLQQRP GKSFKGLIYH GTNLDDEVPS  60
RFSGSGSGAD YSLTISSLES EDFADYYCVQ YAQFPWTFGG GTKLEIK                107

SEQ ID NO: 43          moltype = DNA  length = 363
```

```
FEATURE                 Location/Qualifiers
misc_feature            1..363
                        note = synthesized
source                  1..363
                        mol_type = other DNA
                        organism = synthetic construct
SEQUENCE: 43
gaggtgcagc tggtgcagtc tggagcagag gtgaagaaac caggagagtc tctgaagatc  60
tcctgtaagg gttctggata cagctttagc agttcatgga tcggctgggt gcgccaggca  120
cctgggaaag gcctggaatg gatggggatc atctatcctg atgactctga taccagatac  180
agtccatcct tccaaggcca ggtcaccatc tcagccgaca agtccatcag gactgcctac  240
ctgcagtgga gtagcctgaa ggcctcggac accgctatgt attactgtgc gagacatgtt  300
actatgattt ggggagttat tattgacttc tggggccagg gaaccctggt caccgtctcc  360
tca                                                                363

SEQ ID NO: 44           moltype = AA  length = 121
FEATURE                 Location/Qualifiers
REGION                  1..121
                        note = synthesized
source                  1..121
                        mol_type = protein
                        organism = synthetic construct
SEQUENCE: 44
EVQLVQSGAE VKKPGESLKI SCKGSGYSFS SSWIGWVRQA PGKGLEWMGI IYPDDSDTRY  60
SPSFQGQVTI SADKSIRTAY LQWSSLKASD TAMYYCARHV TMIWGVIIDF WGQGTLVTVS  120
S                                                                  121

SEQ ID NO: 45           moltype = DNA  length = 321
FEATURE                 Location/Qualifiers
misc_feature            1..321
                        note = synthesized
source                  1..321
                        mol_type = other DNA
                        organism = synthetic construct
SEQUENCE: 45
gccatccagt tgacccagtc tccatcctcc ctgtctgcat ctgtaggaga cagagtcacc  60
atcacttgcc gggcaagtca gggcattagc agtgctttag cctggtatca gcagaaacca  120
gggaaagctc ctaagctcct gatctatgat gcctccagtt tggaaagtgg ggtcccatca  180
aggttcagcg gcagtggatc tgggacagat ttcactctca ccatcagcag cctgcagcct  240
gaagattttg caacttatta ctgtcaacag tttaatagtt acccattcac tttcggccct  300
gggaccaaag tggatatcaa a                                            321

SEQ ID NO: 46           moltype = AA  length = 107
FEATURE                 Location/Qualifiers
REGION                  1..107
                        note = synthesized
source                  1..107
                        mol_type = protein
                        organism = synthetic construct
SEQUENCE: 46
AIQLTQSPSS LSASVGDRVT ITCRASQGIS SALAWYQQKP GKAPKLLIYD ASSLESGVPS  60
RFSGSGSGTD FTLTISSLQP EDFATYYCQQ FNSYPFTFGP GTKVDIK                107

SEQ ID NO: 47           moltype = DNA  length = 987
FEATURE                 Location/Qualifiers
misc_feature            1..987
                        note = synthesized
source                  1..987
                        mol_type = other DNA
                        organism = synthetic construct
SEQUENCE: 47
gctagcacca agggcccatc ggtcttcccc ctggcaccct cctccaagag cacctctggg  60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagag agttgagccc  300
aaatcttgtg acaaaactca cacatgccca ccgtgcccag cacctgaagc cgcgggggca  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacaac  540
agcacgtacc gtgtggtcag cgtcctcacc gtcctgcacc aggactggct gaatggcaag  600
gagtacaagt gcgcggtctc caacaaagcc ctcccagccc ccatcgagaa aaccatctcc  660
aaagccaaag ggcagccccg agaaccacag gtgtacaccc tgcccccatc ccgggatgag  720
ctgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctat agcaagctca ccgtggacaa gagcaggtgg  900
cagcagggga acgtcttctc atgctccgtg atgcatgagg ctctgcacaa ccactacacg  960
cagaagagcc tctccctgtc tccgggt                                      987
```

```
SEQ ID NO: 48           moltype = AA  length = 329
FEATURE                 Location/Qualifiers
REGION                  1..329
                        note = synthesized
source                  1..329
                        mol_type = protein
                        organism = synthetic construct
SEQUENCE: 48
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCAVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                  329

SEQ ID NO: 49           moltype = DNA  length = 321
FEATURE                 Location/Qualifiers
misc_feature            1..321
                        note = synthesized
source                  1..321
                        mol_type = other DNA
                        organism = synthetic construct
SEQUENCE: 49
cgtacggtgg ctgcaccatc tgtcttcatc ttcccgccat ctgatgagca gttgaaatct  60
ggaactgcct ctgttgtgtg cctgctgaat aacttctatc ccagagaggc caaagtacag  120
tggaaggtgg ataacgccct ccaatcgggt aactcccagg agagtgtcac agagcaggac  180
agcaaggaca gcacctacag cctcagcagc accctgacgc tgagcaaagc agactacgag  240
aaacacaaag tctacgcctg cgaagtcacc catcagggcc tgagctcgcc cgtcacaaag  300
agcttcaaca ggggagagtg t                                          321

SEQ ID NO: 50           moltype = AA  length = 107
FEATURE                 Location/Qualifiers
REGION                  1..107
                        note = synthesized
source                  1..107
                        mol_type = protein
                        organism = synthetic construct
SEQUENCE: 50
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 51           moltype = DNA  length = 2913
FEATURE                 Location/Qualifiers
misc_feature            1..2913
                        note = synthesized
source                  1..2913
                        mol_type = other DNA
                        organism = synthetic construct
SEQUENCE: 51
gacatccaga tgacccagtc tccatcctcc ctgtctgcat ctgtaggaga cagagtcacc  60
atcacttgcc agtccagtca gagtgtttat aacaacaacg acttagcctg gtatcagcag  120
aaaccaggga aagttcctaa gctcctgatc tattatgctt ccactctggc atctggggtc  180
ccatctcggt tcagtggcag tggatctggg acagatttca ctctcaccat cagcagcctg  240
cagcctgaag atgttgcaac ttattactgt gcaggcggtt atgatacgga tggtcttgat  300
acgtttgctt tcggcggagg gaccaaggtg gagatcaaag gcggtggcgg tagtgggggga  360
ggcggttctg gcggcggagg gtccggcggt ggaggatcag aggtgcagct gttggagtct  420
gggggaggct tggtacagcc tggggggtcc ctgagactct cctgtgcagc ctctggattc  480
accatcagtc gctaccacat gacttgggtc cgccaggctc cagggaaggg gctggagtgg  540
atcggacata tttatgttaa taatgatgac acagactacg cgagctccgc gaaaggccgg  600
ttcaccatct ccagagacaa ttccaagaac acgctgtatc tgcaaatgaa cagcctgaga  660
gccgaggaca cggccaccta tttctgtgcg agattggatg ttggtggtgg tggtgcttat  720
attggggaca tctggggcca gggaactctg gttaccgtct cttcaggcgg tggagggtcc  780
ggcggtggtg gatcccagtc ggtggaggag tctgggggag gcttggtcca gcctgggggg  840
tccctgagac tctcctgtac agcctctgga atcgacctta atacctacga catgatctgg  900
gtccgccagg ctccaggcaa ggggctagag tgggttggaa tcattactta tagtggtagt  960
agatactacg cgaactgggc gaaaggccga ttcaccatct ccaaagacaa taccaagaac  1020
acggtgtatc tgcaaatgaa cagcctgaga gctgaggaca cggctgtgta ttactgtgcc  1080
agagattata tgagtggttc ccacttgtgg ggccagggaa ccctggtcac cgtctctagt  1140
gctagcacca agggcccatc ggtcttcccc ctggcaccct cctccaagag cacctctggg  1200
ggcacagcgg ccctgggctg cctggtcaag gactacttcc ccgaaccggt gacggtgtcg  1260
tggaactcag gcgccctgac cagcggcgtg cacaccttcc cggctgtcct acagtcctca  1320
ggactctact ccctcagcag cgtggtgacc gtgccctcca gcagcttggg cacccagacc  1380
tacatctgca acgtgaatca caagcccagc aacaccaagg tggacaagag agttgagccc  1440
aaatcttgtg acaaaactca cacatgccca ccgtgcccag cacctgaagc cgcgggggca  1500
ccgtcagtct tcctcttccc cccaaaaccc aaggacaccc tcatgatctc ccggacccct  1560
gaggtcacat gcgtggtggt ggacgtgagc cacgaagacc ctgaggtcaa gttcaactgg  1620
tacgtggacg gcgtggaggt gcataatgcc aagacaaagc cgcgggagga gcagtacaac  1680
agcacgtacc gtgtggtcag cgtcctcacc gtcctgcacc aggactggct gaatggcaag  1740
gagtacaagt gcgcggtctc caacaaagcc ctcccagccc ccatcgagaa aaccatctcc  1800
```

```
aaagccaaag ggcagccccg agaaccacag gtgtataccc tgcccccatc ccgggatgag  1860
ctgaccaaga accaggtcag cctgacctgc ctggtcaaag gcttctatcc cagcgacatc  1920
gccgtggagt gggagagcaa tgggcagccg gagaacaact acaagaccac gcctcccgtg  1980
ctggactccg acggctcctt cttcctctat agcaagctca ccgtggacaa gagcaggtgg  2040
cagcagggga acgtcttctc atgctccgtg atgcatgagg ctctgcacaa ccactacacg  2100
cagaagagcc tctccctgtc tccgggtggc ggtggagggt ccggcggtgg tggatccgag  2160
gtgcagctgg tggagtctgg gggaggcttg gtccagcctg gggggtccct gagactctcc  2220
tgtgcagcct ctggattcac catcagtacc aatgcaatga gctgggtccg ccaggctcca  2280
gggaaggggc tggagtggat cggagtcatt actggtcgtg atatcacata ctacgcgagc  2340
tgggcgaaag gcagattcac catctccaga gacaattcca agaacacgct gtatcttcaa  2400
atgaacagcc tgagagccga ggacacggct gtgtattact gtgcgcgcga cggtggatca  2460
tctgctatta ctagtaacaa catttggggc caaggaactc tggtcaccgt ttcttcaggc  2520
ggtggcggta gtgggggagg cggttctggc ggcggagggt ccggcggtgg aggatcagac  2580
gtcgtgatga cccagtctcc ttccaccctg tctgcatctg taggagacag agtcaccatc  2640
aattgccaag ccagtgagag cattagcagt tggttagcct ggtatcagca gaaaccaggg  2700
aaagccccta agctcctgat ctatgaagca tccaaactgg catctggggt cccatcaagg  2760
ttcagcggca gtggatctgg gacagagttc actctcacca tcagcagcct gcagcctgat  2820
gattttgcaa cttattactg ccaaggctat ttttatttta ttagtcgtac ttatgtaaat  2880
tctttcggcg gagggaccaa ggtggagatc aaa                               2913
```

```
SEQ ID NO: 52          moltype = AA  length = 831
FEATURE                Location/Qualifiers
REGION                 1..831
                       note = synthesized
source                 1..831
                       mol_type = protein
                       organism = synthetic construct
SEQUENCE: 52
DIQMTQSPSS LSASVGDRVT ITCQSSQSVY NNNDLAWYQQ KPGKVPKLLI YYASTLASGV  60
PSRFSGSGSG TDFTLTISSL QPEDVATYYC AGGYDTDGLD TFAFGGGTKV EIKGGGGSGG  120
GGSGGGGSGG GGSEVQLLES GGGLVQPGGS LRLSCAASGF TISRYHMTWV RQAPGKGLEW  180
IGHIYVNNDD TDYASSAKGR FTISRDNSKN TLYLQMNSLR AEDTATYFCA RLDVGGGGAY  240
IGDIWGQGTL VTVSSGGGGS GGGGSQSVEE SGGGLVQPGG SLRLSCTASG IDLNTYDMIW  300
VRQAPGKGLE WVGIITYSGS RYYANWAKGR FTISKDNTKN TVYLQMNSLR AEDTAVYYCA  360
RDYMSGSHLW GQGTLVTVSS ASTKGPSVFP LAPSSKSTSG GTAALGCLVK DYFPEPVTVS  420
WNSGALTSGV HTFPAVLQSS GLYSLSSVVT VPSSSLGTQT YICNVNHKPS NTKVDKRVEP  480
KSCDKTHTCP PCPAPEAAGA PSVFLFPPKP KDTLMISRTP EVTCVVVDVS HEDPEVKFNW  540
YVDGVEVHNA KTKPREEQYN STYRVVSVLT VLHQDWLNGK EYKCAVSNKA LPAPIEKTIS  600
KAKGQPREPQ VYTLPPSRDE LTKNQVSLTC LVKGFYPSDI AVEWESNGQP ENNYKTTPPV  660
LDSDGSFFLY SKLTVDKSRW QQGNVFSCSV MHEALHNHYT QKSLSLSPGG GGGSGGGGSD  720
VVMTQSPSTL SASVGDRVTI NCQASESISS WLAWYQQKPG KAPKLLIYEA SKLASGVPSR  780
FSGSGSGTEF TLTISSLQPD DFATYYCQGY FYFISRTYVN SFGGGTKVEI K           831
```

```
SEQ ID NO: 53          moltype = DNA  length = 651
FEATURE                Location/Qualifiers
misc_feature           1..651
                       note = synthesized
source                 1..651
                       mol_type = other DNA
                       organism = synthetic construct
SEQUENCE: 53
gcctatgata tgacccagtc tccatcttcc gtgtctgcat ctgtaggaga cagagtcacc  60
atcaagtgtc aggccagtga ggacatttat agcttcttgg cctggtatca gcagaaacca  120
gggaaagccc ctaagctcct gatccattct gcatcctctc tggcatctgg ggtcccatca  180
aggttcagcg gcagtggatc tgggacagat ttcactctca ccatcagcag cctgcagcct  240
gaagattttg caacttacta ttgtcaacag ggttatggta aaaataatgt tgataatgct  300
ttcggcggag ggaccaaggt ggagatcaaa cgtacggtgg ctgcaccatc tgtcttcatc  360
ttcccgccat ctgatgagca gttgaaatct ggaactgcct ctgttgtgtg cctgctgaat  420
aacttctatc ccagagaggc caaagtacag tggaaggtgg ataacgccct ccaatcgggt  480
aactcccagg agagtgtcac agagcaggac agcaaggaca gcacctacag cctcagcagc  540
accctgacgc tgagcaaagc agactacgag aaacacaaag tctacgcctg cgaagtcacc  600
catcagggcc tgagctcgcc cgtcacaaag agcttcaaca ggggagagtg t           651
```

```
SEQ ID NO: 54          moltype = AA  length = 217
FEATURE                Location/Qualifiers
REGION                 1..217
                       note = synthesized
source                 1..217
                       mol_type = protein
                       organism = synthetic construct
SEQUENCE: 54
AYDMTQSPSS VSASVGDRVT IKCQASEDIY SFLAWYQQKP GKAPKLLIHS ASSLASGVPS  60
RFSGSGSGTD FTLTISSLQP EDFATYYCQQ GYGKNNVDNA FGGGTKVEIK RTVAAPSVFI  120
FPPSDEQLKS GTASVVCLLN NFYPREAKVQ WKVDNALQSG NSQESVTEQD SKDSTYSLSS  180
TLTLSKADYE KHKVYACEVT HQGLSSPVTK SFNRGEC                           217
```